United States Patent
Kikuchi et al.

(10) Patent No.: US 10,214,592 B2
(45) Date of Patent: Feb. 26, 2019

(54) PROTEIN ASSAY METHOD SPECIFIC TO TRACP-5B (TARTRATE RESISTANT ACID PHOSPHATASE 5B)

(71) Applicant: NITTO BOSEKI CO., LTD., Fukushima-shi (JP)

(72) Inventors: Wataru Kikuchi, Koriyama (JP); Kumiko Sasagawa, Koriyama (JP); Kenta Noda, Koriyama (JP)

(73) Assignee: NITTO BOSEKI CO., LTD., Fukushima-shi (JP)

( * ) Notice: Subject to any disclaimer, the term of this patent is extended or adjusted under 35 U.S.C. 154(b) by 0 days.

(21) Appl. No.: 15/505,762

(22) PCT Filed: Aug. 7, 2015

(86) PCT No.: PCT/JP2015/072468
§ 371 (c)(1),
(2) Date: Feb. 22, 2017

(87) PCT Pub. No.: WO2016/027697
PCT Pub. Date: Feb. 25, 2016

(65) Prior Publication Data
US 2017/0267782 A1    Sep. 21, 2017

(30) Foreign Application Priority Data
Aug. 22, 2014  (JP) .................. 2014-168934

(51) Int. Cl.

| | | |
|---|---|---|
| *C07K 16/00* | (2006.01) | |
| *C12P 21/08* | (2006.01) | |
| *C12Q 1/00* | (2006.01) | |
| *C12N 5/07* | (2010.01) | |
| *C12N 5/16* | (2006.01) | |
| *C07K 16/40* | (2006.01) | |
| *C12N 15/00* | (2006.01) | |
| *C12N 15/02* | (2006.01) | |
| *G01N 33/53* | (2006.01) | |
| *G01N 33/543* | (2006.01) | |
| *G01N 33/545* | (2006.01) | |
| *G01N 33/553* | (2006.01) | |
| *G01N 33/577* | (2006.01) | |
| *G01N 33/573* | (2006.01) | |
| *C12N 5/12* | (2006.01) | |
| *C07K 16/18* | (2006.01) | |
| *A61K 39/00* | (2006.01) | |
| *G01N 33/50* | (2006.01) | |
| *C07K 16/30* | (2006.01) | |
| *A61K 38/00* | (2006.01) | |
| *C12N 9/16* | (2006.01) | |

(52) U.S. Cl.
CPC ............ *C07K 16/40* (2013.01); *C12N 5/12* (2013.01); *C12N 5/163* (2013.01); *C12N 15/00* (2013.01); *C12N 15/02* (2013.01); *C12Y 301/03002* (2013.01); *G01N 33/53* (2013.01); *G01N 33/543* (2013.01); *G01N 33/545* (2013.01); *G01N 33/553* (2013.01); *G01N 33/573* (2013.01); *G01N 33/577* (2013.01); *A61K 38/00* (2013.01); *A61K 2039/505* (2013.01); *C07K 16/18* (2013.01); *C07K 16/30* (2013.01); *C07K 2317/14* (2013.01); *C07K 2317/33* (2013.01); *C12N 9/16* (2013.01); *G01N 33/5008* (2013.01); *G01N 2333/916* (2013.01); *G01N 2800/10* (2013.01)

(58) Field of Classification Search
CPC .. A61K 2039/505; A61K 38/00; C07K 16/30; C07K 16/18; G01N 33/5008
See application file for complete search history.

(56) References Cited

U.S. PATENT DOCUMENTS 6,448,027 B1    9/2002  Nakanishi

FOREIGN PATENT DOCUMENTS

| JP | H10-337198 | 12/1998 |
|---|---|---|
| JP | 2001-231595 A1 | 8/2001 |
| JP | 2002-510050 A1 | 4/2002 |
| JP | 2011-524741 A1 | 9/2011 |
| JP | 2013-527836 A1 | 7/2013 |
| WO | WO99/50662 A2 | 10/1999 |
| WO | WO 2012/177972 A1 | 12/2012 |

OTHER PUBLICATIONS

Halleen et al., Calcif. Tissue Int, 2002; 71: 20-25.*
Lloyd et al., Protein Engineering, Design & Selection 2009, 22:159-168.*
A. Janckila, et al.; "Tartrate-resistant Acid Phosphatase Isoform 5b as Serum Marker for Osteoclastic Activity;" Clinical Chemistry; vol. 47; No. 1; 2001; pp. 74-80 (7 Sheets).

(Continued)

*Primary Examiner* — Gary B Nickol
*Assistant Examiner* — Lakia J Jackson-Tongue
(74) *Attorney, Agent, or Firm* — Kratz, Quintos & Hanson, LLP

(57) ABSTRACT

The purpose of the present invention is to provide a monoclonal antibody that is useful in specifically assaying tartrate resistant acid phosphatase 5b (TRACP-5b). A hybridoma producing a monoclonal antibody against TRACP-5b, said monoclonal antibody showing higher reactivity with TRACP-5b than with tartrate resistant acid phosphatase 5a (TRACP-5a) and, therefore, being specific to TRACP-5b, is obtained by cell fusion using, as an antigen, human recombinant TRACP-5b purified from silkworm silk gland. By using this monoclonal antibody, TRACP-5b in a specimen can be highly sensitively and specifically detected.

4 Claims, 8 Drawing Sheets

Specification includes a Sequence Listing.

(56) References Cited

OTHER PUBLICATIONS

T. Onishi; "Study of Human Serum Tartrate-Resistant Acid Phosphatase;" Journal of Nihon University Medical Association; vol. 49; No. 9; 1990; pp. 904-911 (8 Sheets), Abstract only.

K.-H. Lau, et al.; "Characterization and Assay of Tartrate-Resistant Acid Phosphatase Activity in Serum: Potential Use to Assess Bone Resorption;" Clinical Chemistry; vol. 33; No. 4; 1987; pp. 458-462 (5 Sheets).

M. Kraenzlin, et al.; "Development of an Immunoassay for Human Serum Osteoclastic Tartrate-Resistant Acid Phosphatase;" Journal of Clinical Endrocrinology and Metabolism; vol. 71; No. 2; 1990; pp. 442-451 (10 Sheets).

J. Halleen, et al.; "Characterization of Serum Tartrate-Resistant Acid Phosphatase and Development of a Direct Two-Site Immunoassay;" Journal of Bone and Mineral Research; vol. 13; No. 4; 1998; pp. 683-687 (5 Sheets).

H. Bull, et al.; "Reactivity and assay restriction profiles of monoclonal and polyclonal antibodies to acid phosphatases: a preliminary study;" Immunology Letters; vol. 70; 1999; p. 143-149 (7 Sheets).

J. Halleen, et al.; "Two-Site Immunoassays for Osteoclastic Tartrate-Resistant Acid Phosphatase Based on Characterization of Six Monoclonal Antibodies;" Journal of Bone and Mineral Research; vol. 14; No. 3; 1999; pp. 464-469 (6 Sheets).

Y. Nakasato, et al.; "Clinical Significance of Immunoassays for Type-5 Tartrate-resistant Acid Phosphatase;" Clinical Chemistry; vol. 45; No. 12; 1999; pp. 2150-2157 (8 Sheets).

S. Alatalo, et al.; "Rapid Screening Method for Osteoclast Differentiation in Vitro That Measures Tartrate-resistant Acid Phosphatase 5b Activity Secreted into the Culture Medium;" Clinical Chemistry; vol. 46; No. 11; 2000; pp. 1751-1754 (4 Sheets).

A. Janckila, et al.; "Biology and Clinical Significance of Tartrate-Resistant Acid Phosphatases: New Perspective on an Old Enzyme;" Calcif Tissue Int; Nov. 14, 2009; (19 Sheets).

K. Takahashi, et al.; "Electrophoretic study of tartrate-resistant acid phosphatase isoforms in endstage renal disease and rheumatoid arthritis;" Clinica Chimica Acta; vol. 301; 2000; pp. 147-158 (12 Sheets).

J. Halleen, et al.; "Tartrate-Resistant Acid Phosphatase 5b: A Novel Serum Marker of Bone Resorption;" Journal of Bone and Mineral Research; vol. 15; No. 7; 2000; pp. 1337-1345 (9 Sheets).

W. Lam, et al.; "Biochemical Properties of Tartrate-Resistant Acid Phosphatase in Serum of Adults and Children;" Clinical Chemistry; vol. 24; No. 7; 1978; pp. 1105-1108 (4 Sheets).

P. Chamberlain, et al.; "Generation and Characterization of Monoclonal Antibodies to Human Type-5 Tartrate-Resistant Acid Phosphatase: Development of a Specific Immunoassay of the Isoenzyme in Serum;" Clinical Chemistry; vol. 41; No. 10; 1995; pp. 1495-1499 (5 Sheets).

M. Nakanishi, et al.; "Improved method for measuring tartrate-resistant acid phosphatase activity in serum;" Clinical Chemistry; vol. 44; No. 2; 1998; pp. 221-225 (5 Sheets).

S. Miyazaki, et al.; "Development of immunoassays for type-5 tartrate-resistant acid phosphatase in human serum;" Clinica Chimica Acta; vol. 329; 2003; pp. 109-115 (7 Sheets).

A. Janckila, et al.; "Characterization of Monoclonal Antibodies Specific to Human Tartrate-Resistant Acid Phosphatase;" Hybridoma; vol. 16; No. 2; 1997; pp. 175-182 (8 Sheets).

S. Mose, et al.; "Evaluation of Tartrate-resistant Acid Phosphatase (TRACP) 5b as Bone Resorption Marker in Irradiated Bone Metastases;" Anticancer Research; vol. 25; 2005; pp. 4639-4645 (7 Sheets).

International Search Report for International Application No. PCT/JP2015/072468 dated Oct. 20, 2015.

Extended European Search Report for counterpart EP Patent Application No. 15833254.4 dated Oct. 23, 2017 (9 Sheets).

T. Ohashi, et al.; "Development and Characterization of Novel Monoclonal Antibodies Against Tartrate-Resistant Acid Phosphatase 5;" Hybridoma; vol. 25; No. 6; 2006; pp. 358-366 (9 Sheets).

Y. Nishizawa, et al.; "Reference intervals of serum tartrate-resistant acid phosphatase type 5b activity measured with a novel assay in Japanese subjects;" J Bone Miner Metab (2008) 26; pp. 265-270 (6 Sheets).

Chinese Office Action for corresponding Chinese patent application No. 201580051031.2 dated Jan. 23, 2018 (9 Sheets).

* cited by examiner

FIG. 6

ACP5 Translation (325 aa) (SEQ ID NO: 1)

| | | | | | | |
|---|---|---|---|---|---|---|
| 1– | MEMLALLSLL | ATPALRFVA | VGDWGGVPNA | PFHTAREMAN | –50 |
| 51– | AKEIARTVQI | LGADFILSLG | DMFYFTGVQD | INDKRFQETF | EDVFSDRSLR | –100 |
| 101– | KVPWWYVLAGN | HDHLGNVSAQ | IAYSKISKRW | NFPSPFYRLH | FKIPQTNVSV | –150 |
| 151– | AIFMLDTVTL | QPERPRDVKL | ARTDLSWLKK | QLAAAREDYV | –200 |
| 201– | LVAGHYPVWS | IAEHGPTHCL | VKQLRPLLAT | YGVTAYLCGH | DHNLQYLQDE | –250 |
| 251– | NGVGYVLSGA | GNFMDPSKRH | QRKVPNGYLR | FHYGTEDSLG | GFAYVEISSK | –300 |
| 301– | EMTVTYIEAS | GKSLFKTRLP | RRARP | | | |

SUGAR CHAIN POSSIBLE BINDING SITE, CATHEPSIN K SCISSION REGION (SEQ ID NO: 62)

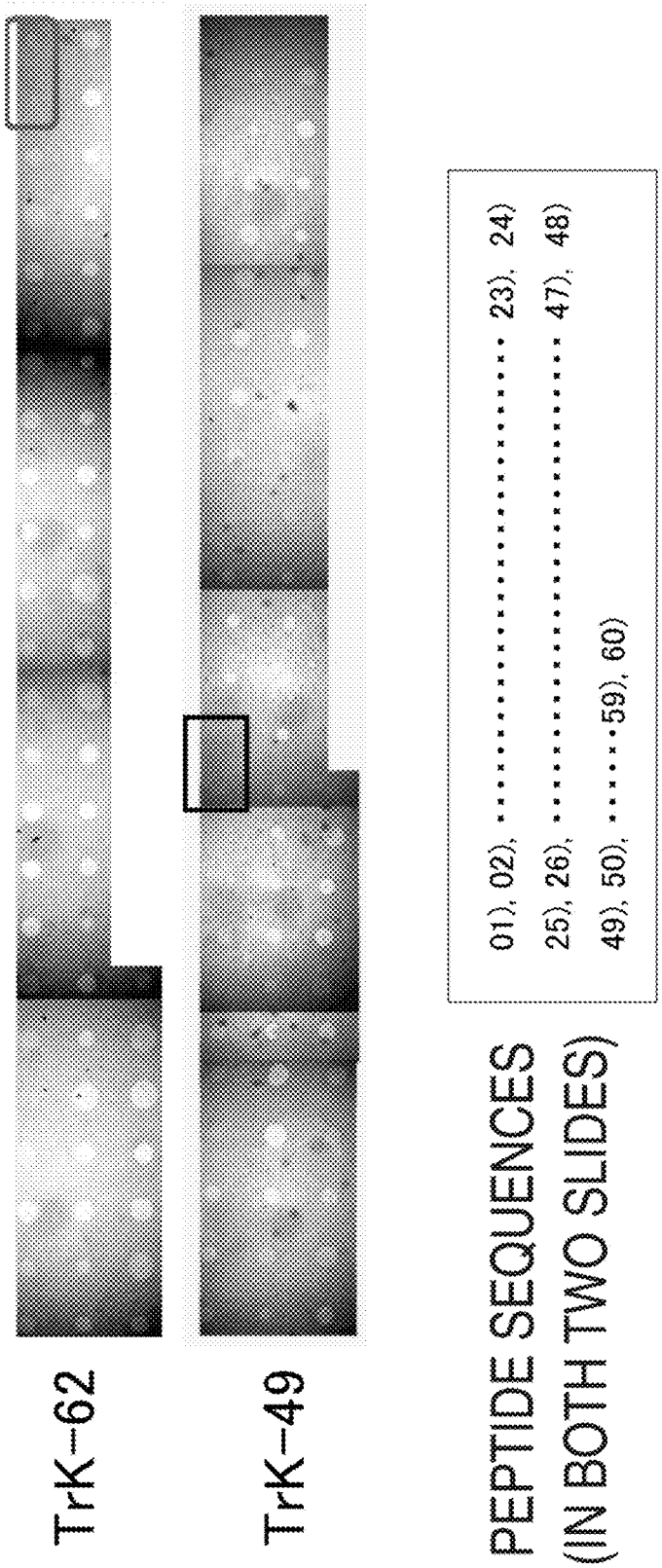

FIG. 8

(SEQ ID NO.: 1)

| | | | | | | |
|---|---|---|---|---|---|---|
| 1- | MDMWTALLIL | QALLLPSLAD | GATPALRFVA | VGDWGGVPNA | PFHTAREMAN | -50 |
| 51- | AKEIARTVQI | LGADFILSLG | DNFYFTGVQD | INDKRFQETF | EDVFSDRSLR | -100 |
| 101- | KVPWYVLAGN | HDHLGNVSAQ | IAYSKISKRW | NFPSPFYRLH | FKIPQTNVSV | -150 |
| 151- | AIFMLDTVTL | CGNSDDFLSQ | QPERPRDVKL | ARTQLSWLKK | QLAAAREDYV | -200 |
| 201- | LVAGHYPVWS | IAEHGPTHCL | VKQLRPLLAT | YGVTAYLCGH | DHNLQYLQDE | -250 |
| 251- | NGVGYVLSGA | GNFMDPSKRH | QRKVPNGYLR | FHYGTEDSLG | GFAYVEISSK | -300 |
| 301- | EMTVTYIEAS | GKSLFKTRLP | RRARP | | | |

SUGAR CHAIN POSSIBLE BINDING SITE

· · · TrK-62 EPITOPE (SEQ ID NO.: 25)
· · · TrK-49 EPITOPE (SEQ ID NO.: 13)
· CATHEPSIN K SCISSION REGION (SEQ ID NO.: 62)

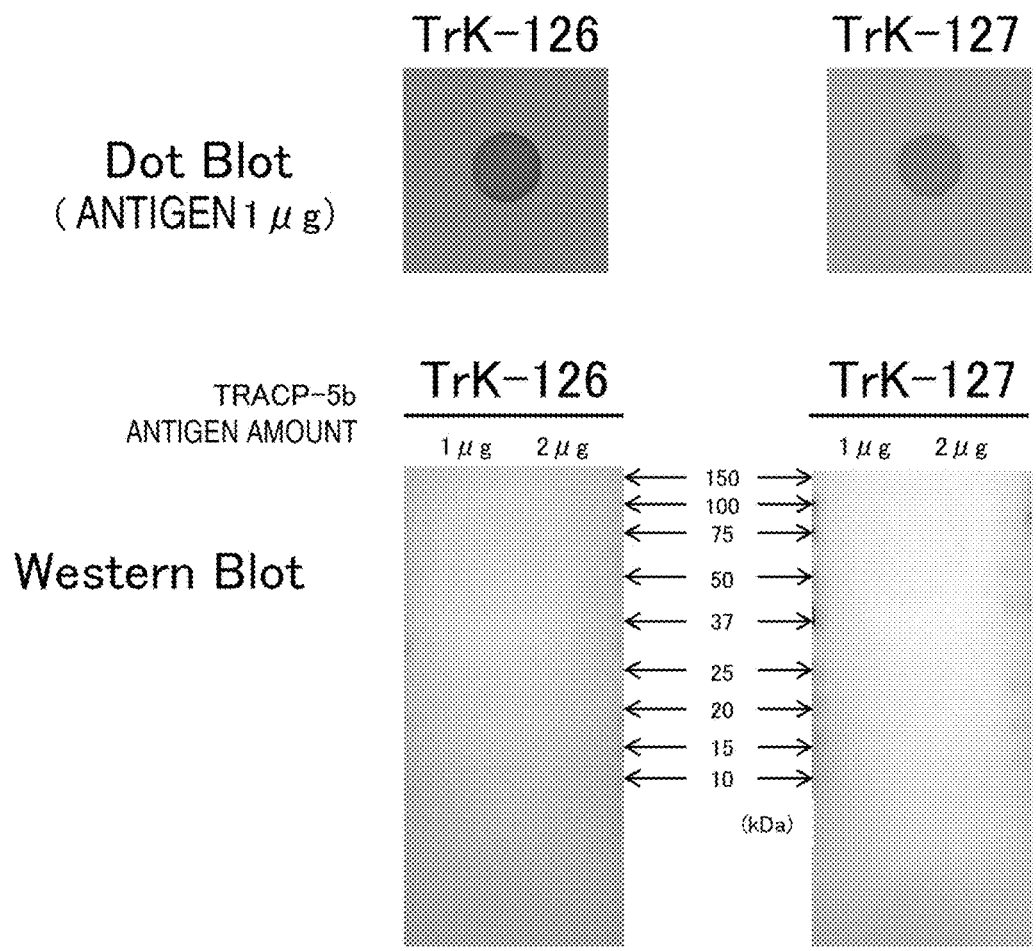

SEQUENCE LISTING

```
<160> NUMBER OF SEQ ID NOS: 62

<210> SEQ ID NO 1
<211> LENGTH: 325
<212> TYPE: PRT
<213> ORGANISM: Homo sapiens

<400> SEQUENCE: 1

Met Asp Met Trp Thr Ala Leu Leu Ile Leu Gln Ala Leu Leu Leu Pro
1               5                   10                  15

Ser Leu Ala Asp Gly Ala Thr Pro Ala Leu Arg Phe Val Ala Val Gly
            20                  25                  30

Asp Trp Gly Gly Val Pro Asn Ala Pro Phe His Thr Ala Arg Glu Met
        35                  40                  45

Ala Asn Ala Lys Glu Ile Ala Arg Thr Val Gln Ile Leu Gly Ala Asp
    50                  55                  60

Phe Ile Leu Ser Leu Gly Asp Asn Phe Tyr Phe Thr Gly Val Gln Asp
65                  70                  75                  80

Ile Asn Asp Lys Arg Phe Gln Glu Thr Phe Glu Asp Val Phe Ser Asp
                85                  90                  95

Arg Ser Leu Arg Lys Val Pro Trp Tyr Val Leu Ala Gly Asn His Asp
            100                 105                 110
```

```
His Leu Gly Asn Val Ser Ala Gln Ile Ala Tyr Ser Lys Ile Ser Lys
            115                 120                 125

Arg Trp Asn Phe Pro Ser Pro Phe Tyr Arg Leu His Phe Lys Ile Pro
130                 135                 140

Gln Thr Asn Val Ser Val Ala Ile Phe Met Leu Asp Thr Val Thr Leu
145                 150                 155                 160

Cys Gly Asn Ser Asp Asp Phe Leu Ser Gln Gln Pro Glu Arg Pro Arg
                165                 170                 175

Asp Val Lys Leu Ala Arg Thr Gln Leu Ser Trp Leu Lys Lys Gln Leu
            180                 185                 190

Ala Ala Ala Arg Glu Asp Tyr Val Leu Val Ala Gly His Tyr Pro Val
        195                 200                 205

Trp Ser Ile Ala Glu His Gly Pro Thr His Cys Leu Val Lys Gln Leu
    210                 215                 220

Arg Pro Leu Leu Ala Thr Tyr Gly Val Thr Ala Tyr Leu Cys Gly His
225                 230                 235                 240

Asp His Asn Leu Gln Tyr Leu Gln Asp Glu Asn Gly Val Gly Tyr Val
                245                 250                 255

Leu Ser Gly Ala Gly Asn Phe Met Asp Pro Ser Lys Arg His Gln Arg
            260                 265                 270

Lys Val Pro Asn Gly Tyr Leu Arg Phe His Tyr Gly Thr Glu Asp Ser
        275                 280                 285

Leu Gly Gly Phe Ala Tyr Val Glu Ile Ser Ser Lys Glu Met Thr Val
    290                 295                 300

Thr Tyr Ile Glu Ala Ser Gly Lys Ser Leu Phe Lys Thr Arg Leu Pro
305                 310                 315                 320

Arg Arg Ala Arg Pro
                325

<210> SEQ ID NO 2
<211> LENGTH: 10
<212> TYPE: PRT
<213> ORGANISM: Artificial sequence
<220> FEATURE:
<223> OTHER INFORMATION: Partial of ACP5

<400> SEQUENCE: 2

Asp Gly Ala Thr Pro Ala Leu Arg Phe Val
1               5                   10

<210> SEQ ID NO 3
<211> LENGTH: 10
<212> TYPE: PRT
<213> ORGANISM: Artificial sequence
<220> FEATURE:
<223> OTHER INFORMATION: Partial of ACP5

<400> SEQUENCE: 3

Ala Leu Arg Phe Val Ala Val Gly Asp Trp
1               5                   10

<210> SEQ ID NO 4
<211> LENGTH: 10
<212> TYPE: PRT
<213> ORGANISM: Artificial sequence
<220> FEATURE:
<223> OTHER INFORMATION: Partial of ACP5

<400> SEQUENCE: 4

Ala Val Gly Asp Trp Gly Gly Val Pro Asn
```

```
<210> SEQ ID NO 5
<211> LENGTH: 10
<212> TYPE: PRT
<213> ORGANISM: Artificial sequence
<220> FEATURE:
<223> OTHER INFORMATION: Partial of ACP5

<400> SEQUENCE: 5

Gly Gly Val Pro Asn Ala Pro Phe His Thr
1               5                   10

<210> SEQ ID NO 6
<211> LENGTH: 10
<212> TYPE: PRT
<213> ORGANISM: Artificial sequence
<220> FEATURE:
<223> OTHER INFORMATION: Partial of ACP5

<400> SEQUENCE: 6

Ala Pro Phe His Thr Ala Arg Glu Met Ala
1               5                   10

<210> SEQ ID NO 7
<211> LENGTH: 10
<212> TYPE: PRT
<213> ORGANISM: Artificial sequence
<220> FEATURE:
<223> OTHER INFORMATION: Partial of ACP5

<400> SEQUENCE: 7

Ala Arg Glu Met Ala Asn Ala Lys Glu Ile
1               5                   10

<210> SEQ ID NO 8
<211> LENGTH: 10
<212> TYPE: PRT
<213> ORGANISM: Artificial sequence
<220> FEATURE:
<223> OTHER INFORMATION: Partial of ACP5

<400> SEQUENCE: 8

Asn Ala Lys Glu Ile Ala Arg Thr Val Gln
1               5                   10

<210> SEQ ID NO 9
<211> LENGTH: 10
<212> TYPE: PRT
<213> ORGANISM: Artificial sequence
<220> FEATURE:
<223> OTHER INFORMATION: Partial of ACP5

<400> SEQUENCE: 9

Ala Arg Thr Val Gln Ile Leu Gly Ala Asp
1               5                   10

<210> SEQ ID NO 10
<211> LENGTH: 10
<212> TYPE: PRT
<213> ORGANISM: Artificial sequence
<220> FEATURE:
<223> OTHER INFORMATION: Partial of ACP5

<400> SEQUENCE: 10

Ile Leu Gly Ala Asp Phe Ile Leu Ser Leu
1               5                   10
```

<210> SEQ ID NO 11
<211> LENGTH: 10
<212> TYPE: PRT
<213> ORGANISM: Artificial sequence
<220> FEATURE:
<223> OTHER INFORMATION: Partial of ACP5

<400> SEQUENCE: 11

Phe Ile Leu Ser Leu Gly Asp Asn Phe Tyr
1               5                   10

<210> SEQ ID NO 12
<211> LENGTH: 10
<212> TYPE: PRT
<213> ORGANISM: Artificial sequence
<220> FEATURE:
<223> OTHER INFORMATION: Partial of ACP5

<400> SEQUENCE: 12

Gly Asp Asn Phe Tyr Phe Thr Gly Val Gln
1               5                   10

<210> SEQ ID NO 13
<211> LENGTH: 10
<212> TYPE: PRT
<213> ORGANISM: Artificial sequence
<220> FEATURE:
<223> OTHER INFORMATION: Partial of ACP5

<400> SEQUENCE: 13

Phe Thr Gly Val Gln Asp Ile Asn Asp Lys
1               5                   10

<210> SEQ ID NO 14
<211> LENGTH: 10
<212> TYPE: PRT
<213> ORGANISM: Artificial sequence
<220> FEATURE:
<223> OTHER INFORMATION: Partial of ACP5

<400> SEQUENCE: 14

Asp Ile Asn Asp Lys Arg Phe Gln Glu Thr
1               5                   10

<210> SEQ ID NO 15
<211> LENGTH: 10
<212> TYPE: PRT
<213> ORGANISM: Artificial sequence
<220> FEATURE:
<223> OTHER INFORMATION: Partial of ACP5

<400> SEQUENCE: 15

Arg Phe Gln Glu Thr Phe Glu Asp Val Phe
1               5                   10

<210> SEQ ID NO 16
<211> LENGTH: 10
<212> TYPE: PRT
<213> ORGANISM: Artificial sequence
<220> FEATURE:
<223> OTHER INFORMATION: Partial of ACP5

<400> SEQUENCE: 16

Phe Glu Asp Val Phe Ser Asp Arg Ser Leu
1               5                   10

```
<210> SEQ ID NO 17
<211> LENGTH: 10
<212> TYPE: PRT
<213> ORGANISM: Artificial sequence
<220> FEATURE:
<223> OTHER INFORMATION: Partial of ACP5

<400> SEQUENCE: 17

Ser Asp Arg Ser Leu Arg Lys Val Pro Trp
1               5                   10

<210> SEQ ID NO 18
<211> LENGTH: 10
<212> TYPE: PRT
<213> ORGANISM: Artificial sequence
<220> FEATURE:
<223> OTHER INFORMATION: Partial of ACP5

<400> SEQUENCE: 18

Arg Lys Val Pro Trp Tyr Val Leu Ala Gly
1               5                   10

<210> SEQ ID NO 19
<211> LENGTH: 10
<212> TYPE: PRT
<213> ORGANISM: Artificial sequence
<220> FEATURE:
<223> OTHER INFORMATION: Partial of ACP5

<400> SEQUENCE: 19

Tyr Val Leu Ala Gly Asn His Asp His Leu
1               5                   10

<210> SEQ ID NO 20
<211> LENGTH: 10
<212> TYPE: PRT
<213> ORGANISM: Artificial sequence
<220> FEATURE:
<223> OTHER INFORMATION: Partial of ACP5

<400> SEQUENCE: 20

Asn His Asp His Leu Gly Asn Val Ser Ala
1               5                   10

<210> SEQ ID NO 21
<211> LENGTH: 10
<212> TYPE: PRT
<213> ORGANISM: Artificial sequence
<220> FEATURE:
<223> OTHER INFORMATION: Partial of ACP5

<400> SEQUENCE: 21

Gly Asn Val Ser Ala Gln Ile Ala Tyr Ser
1               5                   10

<210> SEQ ID NO 22
<211> LENGTH: 10
<212> TYPE: PRT
<213> ORGANISM: Artificial sequence
<220> FEATURE:
<223> OTHER INFORMATION: Partial of ACP5

<400> SEQUENCE: 22

Gln Ile Ala Tyr Ser Lys Ile Ser Lys Arg
1               5                   10
```

```
<210> SEQ ID NO 23
<211> LENGTH: 10
<212> TYPE: PRT
<213> ORGANISM: Artificial sequence
<220> FEATURE:
<223> OTHER INFORMATION: Partial of ACP5

<400> SEQUENCE: 23

Lys Ile Ser Lys Arg Trp Asn Phe Pro Ser
1               5                   10

<210> SEQ ID NO 24
<211> LENGTH: 10
<212> TYPE: PRT
<213> ORGANISM: Artificial sequence
<220> FEATURE:
<223> OTHER INFORMATION: Partial of ACP5

<400> SEQUENCE: 24

Trp Asn Phe Pro Ser Pro Phe Tyr Arg Leu
1               5                   10

<210> SEQ ID NO 25
<211> LENGTH: 10
<212> TYPE: PRT
<213> ORGANISM: Artificial sequence
<220> FEATURE:
<223> OTHER INFORMATION: Partial of ACP5

<400> SEQUENCE: 25

Pro Phe Tyr Arg Leu His Phe Lys Ile Pro
1               5                   10

<210> SEQ ID NO 26
<211> LENGTH: 10
<212> TYPE: PRT
<213> ORGANISM: Artificial sequence
<220> FEATURE:
<223> OTHER INFORMATION: Partial of ACP5

<400> SEQUENCE: 26

His Phe Lys Ile Pro Gln Thr Asn Val Ser
1               5                   10

<210> SEQ ID NO 27
<211> LENGTH: 10
<212> TYPE: PRT
<213> ORGANISM: Artificial sequence
<220> FEATURE:
<223> OTHER INFORMATION: Partial of ACP5

<400> SEQUENCE: 27

Gln Thr Asn Val Ser Val Ala Ile Phe Met
1               5                   10

<210> SEQ ID NO 28
<211> LENGTH: 10
<212> TYPE: PRT
<213> ORGANISM: Artificial sequence
<220> FEATURE:
<223> OTHER INFORMATION: Partial of ACP5

<400> SEQUENCE: 28

Val Ala Ile Phe Met Leu Asp Thr Val Thr
1               5                   10

<210> SEQ ID NO 29
```

<211> LENGTH: 10
<212> TYPE: PRT
<213> ORGANISM: Artificial sequence
<220> FEATURE:
<223> OTHER INFORMATION: Partial of ACP5

<400> SEQUENCE: 29

Leu Asp Thr Val Thr Leu Cys Gly Asn Ser
1               5                   10

<210> SEQ ID NO 30
<211> LENGTH: 10
<212> TYPE: PRT
<213> ORGANISM: Artificial sequence
<220> FEATURE:
<223> OTHER INFORMATION: Partial of ACP5

<400> SEQUENCE: 30

Leu Cys Gly Asn Ser Asp Asp Phe Leu Ser
1               5                   10

<210> SEQ ID NO 31
<211> LENGTH: 10
<212> TYPE: PRT
<213> ORGANISM: Artificial sequence
<220> FEATURE:
<223> OTHER INFORMATION: Partial of ACP5

<400> SEQUENCE: 31

Asp Asp Phe Leu Ser Gln Gln Pro Glu Arg
1               5                   10

<210> SEQ ID NO 32
<211> LENGTH: 10
<212> TYPE: PRT
<213> ORGANISM: Artificial sequence
<220> FEATURE:
<223> OTHER INFORMATION: Partial of ACP5

<400> SEQUENCE: 32

Gln Gln Pro Glu Arg Pro Arg Asp Val Lys
1               5                   10

<210> SEQ ID NO 33
<211> LENGTH: 10
<212> TYPE: PRT
<213> ORGANISM: Artificial sequence
<220> FEATURE:
<223> OTHER INFORMATION: Partial of ACP5

<400> SEQUENCE: 33

Pro Arg Asp Val Lys Leu Ala Arg Thr Gln
1               5                   10

<210> SEQ ID NO 34
<211> LENGTH: 10
<212> TYPE: PRT
<213> ORGANISM: Artificial sequence
<220> FEATURE:
<223> OTHER INFORMATION: Partial of ACP5

<400> SEQUENCE: 34

Leu Ala Arg Thr Gln Leu Ser Trp Leu Lys
1               5                   10

<210> SEQ ID NO 35
<211> LENGTH: 10

```
<212> TYPE: PRT
<213> ORGANISM: Artificial sequence
<220> FEATURE:
<223> OTHER INFORMATION: Partial of ACP5

<400> SEQUENCE: 35

Leu Ser Trp Leu Lys Lys Gln Leu Ala Ala
1               5                   10

<210> SEQ ID NO 36
<211> LENGTH: 10
<212> TYPE: PRT
<213> ORGANISM: Artificial sequence
<220> FEATURE:
<223> OTHER INFORMATION: Partial of ACP5

<400> SEQUENCE: 36

Lys Gln Leu Ala Ala Ala Arg Glu Asp Tyr
1               5                   10

<210> SEQ ID NO 37
<211> LENGTH: 10
<212> TYPE: PRT
<213> ORGANISM: Artificial sequence
<220> FEATURE:
<223> OTHER INFORMATION: Partial of ACP5

<400> SEQUENCE: 37

Ala Arg Glu Asp Tyr Val Leu Val Ala Gly
1               5                   10

<210> SEQ ID NO 38
<211> LENGTH: 10
<212> TYPE: PRT
<213> ORGANISM: Artificial sequence
<220> FEATURE:
<223> OTHER INFORMATION: Partial of ACP5

<400> SEQUENCE: 38

Val Leu Val Ala Gly His Tyr Pro Val Trp
1               5                   10

<210> SEQ ID NO 39
<211> LENGTH: 10
<212> TYPE: PRT
<213> ORGANISM: Artificial sequence
<220> FEATURE:
<223> OTHER INFORMATION: Partial of ACP5

<400> SEQUENCE: 39

His Tyr Pro Val Trp Ser Ile Ala Glu His
1               5                   10

<210> SEQ ID NO 40
<211> LENGTH: 10
<212> TYPE: PRT
<213> ORGANISM: Artificial sequence
<220> FEATURE:
<223> OTHER INFORMATION: Partial of ACP5

<400> SEQUENCE: 40

Ser Ile Ala Glu His Gly Pro Thr His Cys
1               5                   10

<210> SEQ ID NO 41
<211> LENGTH: 10
<212> TYPE: PRT
```

```
<213> ORGANISM: Artificial sequence
<220> FEATURE:
<223> OTHER INFORMATION: Partial of ACP5

<400> SEQUENCE: 41

Gly Pro Thr His Cys Leu Val Lys Gln Leu
1               5                   10

<210> SEQ ID NO 42
<211> LENGTH: 10
<212> TYPE: PRT
<213> ORGANISM: Artificial sequence
<220> FEATURE:
<223> OTHER INFORMATION: Partial of ACP5

<400> SEQUENCE: 42

Leu Val Lys Gln Leu Arg Pro Leu Leu Ala
1               5                   10

<210> SEQ ID NO 43
<211> LENGTH: 10
<212> TYPE: PRT
<213> ORGANISM: Artificial sequence
<220> FEATURE:
<223> OTHER INFORMATION: Partial of ACP5

<400> SEQUENCE: 43

Arg Pro Leu Leu Ala Thr Tyr Gly Val Thr
1               5                   10

<210> SEQ ID NO 44
<211> LENGTH: 10
<212> TYPE: PRT
<213> ORGANISM: Artificial sequence
<220> FEATURE:
<223> OTHER INFORMATION: Partial of ACP5

<400> SEQUENCE: 44

Thr Tyr Gly Val Thr Ala Tyr Leu Cys Gly
1               5                   10

<210> SEQ ID NO 45
<211> LENGTH: 10
<212> TYPE: PRT
<213> ORGANISM: Artificial sequence
<220> FEATURE:
<223> OTHER INFORMATION: Partial of ACP5

<400> SEQUENCE: 45

Ala Tyr Leu Cys Gly His Asp His Asn Leu
1               5                   10

<210> SEQ ID NO 46
<211> LENGTH: 10
<212> TYPE: PRT
<213> ORGANISM: Artificial sequence
<220> FEATURE:
<223> OTHER INFORMATION: Partial of ACP5

<400> SEQUENCE: 46

His Asp His Asn Leu Gln Tyr Leu Gln Asp
1               5                   10

<210> SEQ ID NO 47
<211> LENGTH: 10
<212> TYPE: PRT
<213> ORGANISM: Artificial sequence
```

```
<220> FEATURE:
<223> OTHER INFORMATION: Partial of ACP5

<400> SEQUENCE: 47

Gln Tyr Leu Gln Asp Glu Asn Gly Val Gly
1               5                   10

<210> SEQ ID NO 48
<211> LENGTH: 10
<212> TYPE: PRT
<213> ORGANISM: Artificial sequence
<220> FEATURE:
<223> OTHER INFORMATION: Partial of ACP5

<400> SEQUENCE: 48

Glu Asn Gly Val Gly Tyr Val Leu Ser Gly
1               5                   10

<210> SEQ ID NO 49
<211> LENGTH: 10
<212> TYPE: PRT
<213> ORGANISM: Artificial sequence
<220> FEATURE:
<223> OTHER INFORMATION: Partial of ACP5

<400> SEQUENCE: 49

Tyr Val Leu Ser Gly Ala Gly Asn Phe Met
1               5                   10

<210> SEQ ID NO 50
<211> LENGTH: 10
<212> TYPE: PRT
<213> ORGANISM: Artificial sequence
<220> FEATURE:
<223> OTHER INFORMATION: Partial of ACP5

<400> SEQUENCE: 50

Ala Gly Asn Phe Met Asp Pro Ser Lys Arg
1               5                   10

<210> SEQ ID NO 51
<211> LENGTH: 10
<212> TYPE: PRT
<213> ORGANISM: Artificial sequence
<220> FEATURE:
<223> OTHER INFORMATION: Partial of ACP5

<400> SEQUENCE: 51

Asp Pro Ser Lys Arg His Gln Arg Lys Val
1               5                   10

<210> SEQ ID NO 52
<211> LENGTH: 10
<212> TYPE: PRT
<213> ORGANISM: Artificial sequence
<220> FEATURE:
<223> OTHER INFORMATION: Partial of ACP5

<400> SEQUENCE: 52

His Gln Arg Lys Val Pro Asn Gly Tyr Leu
1               5                   10

<210> SEQ ID NO 53
<211> LENGTH: 10
<212> TYPE: PRT
<213> ORGANISM: Artificial sequence
<220> FEATURE:
```

<223> OTHER INFORMATION: Partial of ACP5

<400> SEQUENCE: 53

Pro Asn Gly Tyr Leu Arg Phe His Tyr Gly
1               5                   10

<210> SEQ ID NO 54
<211> LENGTH: 10
<212> TYPE: PRT
<213> ORGANISM: Artificial sequence
<220> FEATURE:
<223> OTHER INFORMATION: Partial of ACP5

<400> SEQUENCE: 54

Arg Phe His Tyr Gly Thr Glu Asp Ser Leu
1               5                   10

<210> SEQ ID NO 55
<211> LENGTH: 10
<212> TYPE: PRT
<213> ORGANISM: Artificial sequence
<220> FEATURE:
<223> OTHER INFORMATION: Partial of ACP5

<400> SEQUENCE: 55

Thr Glu Asp Ser Leu Gly Gly Phe Ala Tyr
1               5                   10

<210> SEQ ID NO 56
<211> LENGTH: 10
<212> TYPE: PRT
<213> ORGANISM: Artificial sequence
<220> FEATURE:
<223> OTHER INFORMATION: Partial of ACP5

<400> SEQUENCE: 56

Gly Gly Phe Ala Tyr Val Glu Ile Ser Ser
1               5                   10

<210> SEQ ID NO 57
<211> LENGTH: 10
<212> TYPE: PRT
<213> ORGANISM: Artificial sequence
<220> FEATURE:
<223> OTHER INFORMATION: Partial of ACP5

<400> SEQUENCE: 57

Val Glu Ile Ser Ser Lys Glu Met Thr Val
1               5                   10

<210> SEQ ID NO 58
<211> LENGTH: 10
<212> TYPE: PRT
<213> ORGANISM: Artificial sequence
<220> FEATURE:
<223> OTHER INFORMATION: Partial of ACP5

<400> SEQUENCE: 58

Lys Glu Met Thr Val Thr Tyr Ile Glu Ala
1               5                   10

<210> SEQ ID NO 59
<211> LENGTH: 10
<212> TYPE: PRT
<213> ORGANISM: Artificial sequence
<220> FEATURE:
<223> OTHER INFORMATION: Partial of ACP5

```
<400> SEQUENCE: 59

Thr Tyr Ile Glu Ala Ser Gly Lys Ser Leu
1               5                   10

<210> SEQ ID NO 60
<211> LENGTH: 10
<212> TYPE: PRT
<213> ORGANISM: Artificial sequence
<220> FEATURE:
<223> OTHER INFORMATION: Partial of ACP5

<400> SEQUENCE: 60

Ser Gly Lys Ser Leu Phe Lys Thr Arg Leu
1               5                   10

<210> SEQ ID NO 61
<211> LENGTH: 11
<212> TYPE: PRT
<213> ORGANISM: Artificial sequence
<220> FEATURE:
<223> OTHER INFORMATION: Partial of ACP5

<400> SEQUENCE: 61

Phe Lys Thr Arg Leu Pro Arg Arg Ala Arg Pro
1               5                   10

<210> SEQ ID NO 62
<211> LENGTH: 20
<212> TYPE: PRT
<213> ORGANISM: Artificial sequence
<220> FEATURE:
<223> OTHER INFORMATION: Partial of ACP5

<400> SEQUENCE: 62

Gly Asn Ser Asp Asp Phe Leu Ser Gln Gln Pro Glu Arg Pro Arg Asp
1               5                   10                  15

Val Lys Leu Ala
            20
```

PROTEIN ASSAY METHOD SPECIFIC TO TRACP-5B (TARTRATE RESISTANT ACID PHOSPHATASE 5B)

INCORPORATION BY REFERENCE OF SEQUENCE LISTING

Applicant hereby incorporates by reference the electronically filed sequence listing, which is computer-readable file "170057AmendedsequencelistingW732300ST25.txt". This file was created on Sep. 27, 2018, and is of size 14.8 kB.

TECHNICAL FIELD

The present invention relates to a monoclonal antibody specific to tartrate resistant acid phosphatase 5b (TRACP-5b; also known as osteoclast-derived tartrate resistant acid phosphatase), a hybridoma producing the monoclonal antibody, a method for detecting TRACP-5b using the monoclonal antibody and a kit for the method.

The monoclonal antibody according to the present invention is extremely effective as a marker for bone resorption in the field of medical treatment and clinical laboratory diagnosis for bone disease.

BACKGROUND ART

The tartrate resistant acid phosphatases (TRACP: EC3.1.3.2) in the serum are acid phosphatases which are mostly derived from osteoclasts. The measurement of acid phosphatases is useful as an index for evaluating the function of osteoclasts, and the acid phosphatases therefore attract attention as a bone resorption marker (Non Patent Literature 1). In the meantime, the acid phosphatase in the serum is analyzed by polyacrylamide gel electrophoresis to provide 6 bands (0 to 5 from an original point). Of these bands, the substance of the 5th band exhibits resistance to tartrate and thus called Band 5 tartrate resistant acid phosphatase (TRACP5). TRACP5 is further electrophoretically divided into TRACP 5a, which often binds to sialic acid of a sugar chain and TRACP 5b, which does not virtually bind to sialic acid. TRACP 5a is an enzyme derived from platelets and others and exhibit a constant blood level; whereas, the blood level of TRACP 5b alone varies in accordance with bone resorption. It is therefore considered that TRACP 5b is a tartrate resistant acid phosphatase itself derived from osteoclasts (Patent Literature 1).

Note that, also in Clinical Chemistry (Non Patent Literature 2), it is recommended that ACP derived from osteoclasts is abbreviated as TRACP-5b. Thus, in the specification, ACP, which is derived from osteoclasts and used as an index of bone resorption, is referred to as TRACP-5b. Tartrate resistant acid phosphatase derived from osteoclasts and tartrate resistant acid phosphatase 5b, which are regarded as synonym, are expressed as TRACP-5b.

Conventional activity measurement methods for obtaining TRACP (acid phosphatase) activity used as an index representing the activity of osteoclasts have a problem in specificity, sensitivity, intricate measurement process and measurement time.

Generally in measurement of TRACP-5b by an activity measurement method, the activity of the enzyme is obtained by subjecting a synthetic substrate, i.e., a phosphoric acid ester, to an enzymatic reaction in the presence of tartaric acid and colorimetrically determining the amount of resultant reaction product (alcohol or phenol). At this time, since tartaric acid inhibits prostate-derived acid phosphatase, the activity of the remaining acid phosphatase is measured by using a substrate to obtain the TRACP activity, which is regarded as TRACP-5b activity. However, erythrocyte-derived and platelet-derived tartrate resistant acid phosphatases present in a specimen except osteoclast-derived tartrate resistant acid phosphatase are also measured herein. Thus, specificity is a problem herein. To improve this method, a method of pretreating a solution obtained by diluting the serum 5 fold by incubating it at 37° C. for one hour and thereafter and measuring the remaining TRACP activity by using p-nitrophenyl phosphate (pNPP) as a substrate, in the presence of tartaric acid (Non Patent Literature 3 and Non Patent Literature 4) is known. In this method, the effect of the erythrocyte-derived acid phosphatase can be avoided, however, the effect of the platelet-derived acid phosphatase cannot be eliminated. The present inventors have reported, as a method for further more specifically measuring the activity, a TRACP-5b measurement method (Patent Literature 2), which uses difference in sensitivity to fluorine between activities of TRACP-5b and erythrocyte/platelet-derived tartrate resistant acid phosphatases. However, the effects of erythrocyte/platelet-derived tartrate resistant acid phosphatases are avoided but the effect of TRACP-5a cannot be eliminated. In addition, TRACP-5b activity is obtained by subtracting the activity not inhibited in the presence of fluorine from the total activity of the tartrate resistant acid phosphatases. Thus, accuracy is another point of improvement to be desired. Furthermore, a method of more specifically measuring TRACP-5b activity was reported to be established by using the method employing fluorine in combination with a TRACP-5a inhibitor (Patent Literature 3). However, although specificity is improved compared to the method employing fluorine alone, osteoclast-derived TRACP-5b activity is obtained computationally by subtraction. For the reason, accuracy still remains as a problem.

Human TRACP-5α and TRACP-5b, both of which are isoforms derived from human ACP5 gene product constituted of 325 amino acids (SEQ. ID No. 1). TRACY-5a is formed by removing a secretory signal sequence consisting of $1^{st}$ to $21^{st}$ amino acids; whereas, TRACP-5b is formed by further removing a peptide consisting of the $162^{nd}$ to $181^{st}$ amino acids by cathepsin K and connecting resultant subunit structures of about 16 kDa and about 23 kDa via a S—S bond between the $161^{st}$ cysteine and the $219^{th}$ cysteine.

As an immunological method for measuring TRACP-5b, immunoassays using a polyclonal antibody and a monoclonal antibody are known (Non Patent Literature 5, Non Patent Literature 6, Non Patent Literature 7, Non Patent Literature 8, Non Patent Literature 9 and Non Patent Literature 10). Since TRACP-5a and TRACP-5b are collectively measured in these assays, the effect of TRACP-5a cannot be ignored (Non Patent Literature 11). Another immunological method for more specifically measuring TRACP-5b has been reported (Patent Literature 4). This method more specifically measures TRACP-5b activity; however, the antibody used in measurement is not specific to TRACP-5b and reacts also with TRACP-5a, resulting in that the activity is measured by taking advantage of difference in optimal pH between TRACP-5a and TRACP-5b and a measurement value was computationally obtained. Therefore, in a specimen from a patient with e.g., an end-stage renal disease in which TRACP-5a is enhanced, the effect is concerned. Furthermore, since the difference between a specimen of a healthy person and a specimen of a patient whose bone resorption is enhanced is small, sensitivity as a bone resorption marker is not sufficient (Non Patent Literature 12).

The present inventors previously formed a monoclonal antibody which can distinguishably recognize TRACP-5a and TRACP-5b (Patent Literature 6). As a result, they successfully formed an antibody having a certain selectivity; however, there is room for improvement in selectivity and a further improvement is required for clinical trials.

CITATION LIST

Patent Literature

Patent Literature 1: JP 2002-510050 A
Patent Literature 2: JP 10-337198 A
Patent Literature 3: JP 2001-231595 A
Patent Literature 4: WO99/50662
Patent Literature 5: JP 2002-510050 A
Patent Literature 6: Japanese Patent No. 4164804

Non Patent Literature

Non Patent Literature 1: Bone metabolism marker, edited by Masao Fukunaga, Toshitaka Nakamura and Toshio Matsumoto, Medical View, 1995
Non Patent Literature 2: Clin. Chem. 47: 1497, 2001
Non Patent Literature 3: Journal of Nihon University Medical Association. 49: 904-911, 1990
Non Patent Literature 4: Clin. Chem. 33: 458-462, 1987
Non Patent Literature 5: J Clin Endocrinol Metab. 71: 442-451, 1990
Non Patent Literature 6: J Bone Miner Res. 13: 683-687, 1998
Non Patent Literature 7: Immunol Lett. 70: 143-149, 1999
Non Patent Literature 8: J Bone Miner Res. 14: 464-469, 1999
Non Patent Literature 9: Clin Chem. 45: 2150-2157, 1999
Non Patent Literature 10: Clin Chem. 46: 1751-1754, 2000
Non Patent Literature 11: Calcif Tissue Int, on line 14, September, 2009
Non Patent Literature 12: Clin. Chim. Acta 301: 147-158, 2000

SUMMARY OF INVENTION

Technical Problem

In view of the aforementioned problems, the present invention is directed to providing a monoclonal antibody having further higher specificity and affinity for a bone resorption marker, i.e., an osteoclast-derived tartrate resistant acid phosphatase (TRACP-5b), a hybridoma producing the same, a method for detecting TRACP-5b by using the monoclonal antibody and a kit for use in the method.

Solution to Problem

To solve a problem of recognizing the above-mentioned TRACP-5 isoforms different in sugar-chain modification, the present inventors obtained monoclonal antibodies having high specificity and affinity not by using human-derived TRACP-5b but by purposely using recombinant human TRACP-5b produced in a silk gland of silkworm having different sugar chain modification form a human, and analyzed the obtained antibodies.

The embodiments of the present invention are more specifically as described in [1] to [28].

[1] A monoclonal antibody recognizing an epitope based on a steric structure of TRACP-5b and not recognizing any of epitopes formed of its primary structure of linear sequence;
[2] Hybridoma TrK-126 of Accession number NITE BP-01866;
[3] Hybridoma TrK-127 of Accession number NITE BP-01867;
[4] The monoclonal antibody according to [1] produced by the hybridoma of [2];
[5] The monoclonal antibody according to [1] produced by the hybridoma of [3];
[6] A TRACP-5b detection method for detecting TRACP-5b in a specimen by an immunoassay using one or more monoclonal antibodies according to [1];
[7] The TRACP-5b detection method according to [6], in which TRACP-5b in a specimen is detected by an immunoassay using the monoclonal antibodies according to [4] and [5];
[8] The detection method according to [7], in which TRACP-5b in a specimen is detected by sandwich ELISA assay using the monoclonal antibody according to [4] and the monoclonal antibody according to [5];
[9] The detection method according to [7], in which TRACP-5b in a specimen is detected by a chemiluminescent enzyme immunoassay (CLEIA) using the monoclonal antibody according to [4] and the monoclonal antibody according to [5];
[10] The detection method according to [7], in which TRACP-5b in a specimen is detected by a latex agglutination method (nephelometry or turbidimetry) using the monoclonal antibody according to [4] and the monoclonal antibody according to [5];
[11] The detection method according to any one of [6] to [10], wherein TRACP-5b is used as a bone resorption marker in clinical laboratory testing for bone disease.
[12] A kit for use in detection of TRACP-5b, comprising the one or more monoclonal antibodies according to [1] as a constituent;
[13] A kit for use in detection of TRACP-5b comprising the monoclonal antibody according to [4] and the monoclonal antibody according to [5] as constituents;
[14] A kit for use in the detection method according to [8], comprising:
(1) a solid support,
(2) the monoclonal antibody according to [4], the monoclonal antibody according to [5] labeled; or the monoclonal antibody according to [5] and the monoclonal antibody according to [4] labeled, and
(3) a component for detecting the label, as constituents;
[15] A kit for use in the detection method according to [9], comprising:
(1) a magnetic bead,
(2) the monoclonal antibody according to [4], the monoclonal antibody according to [5] labeled; or the monoclonal antibody according to [5] and the monoclonal antibody according to [4] labeled, and
(3) a component for detecting the label, as constituents;
[16] A kit for use in the detection method according to [10], comprising:
(1) a latex particle, and
(2) the monoclonal antibody according to [4] and the monoclonal antibody according to [5], as constituents.
[17] A monoclonal antibody against recombinant human TRACP-5b as an antigen, recognizing an epitope based on a steric structure of TRACP-5b and not recognizing any epitope formed of its primary structure of linear sequence, wherein the recombinant human TRACP-5b is produced in a silk gland of a silkworm and modified with a silkworm-specific sugar chain;

[18] The antibody according to [17], produced by the hybridoma according to [2] or [3];

[19] The monoclonal antibody according to [17] or [18], which does not substantially exhibit cross-reactivity to acid phosphatases derived from an erythrocyte, a platelet, a neutrophil and prostate.

[20] A TRACP-5b detection method for detecting TRACP-5b in a specimen by an immunoassay using any one of the monoclonal antibodies according to [17] to [19];

[21] The detection method according to [20] for detecting TRACP-5b in a specimen by sandwich assay ELISA using any one of monoclonal antibodies according to [17] to [19];

[22] The detection method according to [20] for detecting TRACP-5b in a specimen by a chemiluminescent enzyme immunoassay (CLEIA) using any one of monoclonal antibodies according to [17] to [19];

[23] The detection method according to [20] for detecting TRACP-5b in a specimen by a latex agglutination method (nephelometry or turbidimetry) using any one of the monoclonal antibodies according to [17] to [19];

[24] The detection method according to any one of [20] to [23], wherein TRACP-5b is used as a bone resorption marker in clinical laboratory testing for bone disease.

[25] A kit for use in detection of TRACP-5b, comprising the monoclonal antibody according to any one of [17] to [19] as a constituent;

[26] A kit for use in the detection method according to [21], comprising a solid support, the monoclonal antibody according to any one of [17] to [19], another labeled antibody against TRACP-5b and a component for detecting the label, as constituents;

[27] A kit for use in the detection method according to [22], comprising a magnetic bead, the monoclonal antibody according to any one of [17] to [19] and another labeled antibody against TRACP-5b and a component for detecting the label, as constituents;

[28] A kit for use in the detection method according to [23], comprising a latex particle; and the monoclonal antibody according to any one of [17] to [19], as constituents.

Advantageous Effects of Invention

The present invention makes it possible to more efficiently detect and quantify TRACP-5b in a biological sample than conventional methods. The present invention can contribute to diagnosis of various diseases.

BRIEF DESCRIPTION OF DRAWINGS

FIG. 6 shows the amino acid sequence of ACP5 (TRACP-5) and various possible modification sites.
FIG. 7 shows epitope mapping of Trk-62 and Trk-49 according to <Comparative Example>.
FIG. 8 shows epitope sites of Trk-62 and Trk-49 according to <Comparative Example>.
FIG. 10 shows dot blotting and Western blotting of TRACP-5b using Trk-126 and Trk-127.

DESCRIPTION OF EMBODIMENTS

Figure 1:
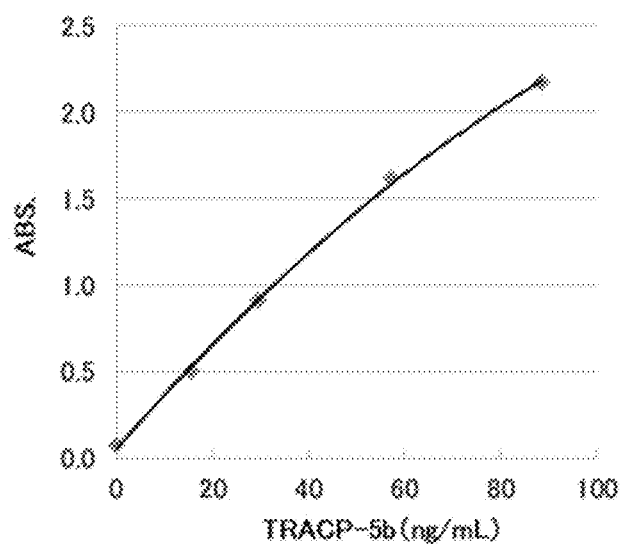
FIG. 1 shows measurement of TRACP-5b by ELISA.

The monoclonal antibody of the present invention can be obtained by using a recombinant human TRACP-5b as an immunogen. In Examples described later in the specification, the recombinant human TRACP-5b was purified from a genetic recombinant silkworm; however, a host is not limited as long as it can express human TRACP-5b. For example, cultured cells and *E. coli* can be used.

The monoclonal antibody of the present invention is produced by a hybridoma obtained by immunizing an animal with, for example, purified human TRACP-5b as an immunogen, and fusing an anti-human TRACP-5b antibody-producing cell produced by the animal with a bone marrow tumor cell.

The hybridoma can be obtained by the following method: human TRACP-5b obtained as mentioned above is mixed with an adjuvant already known in the art, such as Freund's complete/incomplete adjuvant, aluminum hydroxide adjuvant and pertussis adjuvant, to prepare an adjuvant solution for sensitization; and an animal, such as a mouse and a rat, is immunized by administering the adjuvant solution, several times at intervals of 1 to 3 weeks, intraperitoneally, subcutaneously or through a tail vein. The antigen amount for sensitization falls within the range of 1 µg to 100 mg and usually preferably about 50 µg. The number of immunization times is usually 2 to 7; however various methods are known. Subsequently, an antibody-producing cell derived from e.g., spleen and a cell capable of proliferating in a test tube, such as a bone marrow tumor cell (myeloma cell), are fused. The antibody-producing cell can be obtained from e.g., spleen of an animal such as a mouse, a nude mouse and a rat.

As the above fusion technique, a standard method of Kohler and Milstein (Nature, 256, 495, 1975) known in the art is used where fusion can be made by using polyethylene glycol (PEG). Fusion can be also made by employing Sendai virus and an electric fusion method.

A hybridoma producing an antibody recognizing human TRACP-5b from the fused cells can be selected by the following method. The fused cells are subjected to limiting dilution and cultured in HAT medium and HT medium. From the resultant colonies formed of surviving cells, a hybridoma is selected. If an antibody against human TRACP-5b is contained in the supernatant of culture of a colony of the fused cell seeded in e.g., 96 wells, the supernatant is placed on an assay plate on which human TRACP-5b is immobilized. After completion of a reaction, a labeled secondary antibody such as an anti-mouse immunoglobulin antibody labeled with HRP is allowed to react in accordance with ELISA. In this manner, a clone producing a monoclonal antibody against human TRACP-5b can be selected. Instead of HRP, an enzyme such as an alkaline phosphatase, a fluorescent substance and a radioactive materiale can also be used as the labeling substance attached to a labeled antibody. Furthermore, a control assay plate to which BSA as a blocking agent alone is bound, is simultaneously subjected to ELISA. In this manner, an antibody specific to human TRACP-5b can be screened. In other words, a clone giving a positive response to the human TRACP-5b plate and a negative response to BSA by ELISA can be selected.

As the hybridoma of the present invention, a hybridoma, which produces a monoclonal antibody particularly reacting with human TRACP-5b and not cross-reacting with acid phosphatases derived from erythrocytes, platelets, neutrophils and prostate, is desirably selected from the hybridomas producing monoclonal antibodies recognizing human TRACP-5b.

In particular, the monoclonal antibody of the present invention is preferably a monoclonal antibody, which does not bind to human TRACP-5a in a detection system; and recognizes and binds to TRACP-5b alone, in order that the results of clinical laboratory testing with the antibody more definitely indicate bone resorption.

The phrase "binds to human TRACP-5b and does not bind to human TRACP-5a" means that, in a detection system used in the technical field (e.g., sandwich ELISA assay), reactivity to human TRACP-5b in the detection system is about 100 times or more, more preferably about 500 times or more, higher than the reactivity to human TRACP-5a.

The hybridoma is cultured in a medium usually used for culturing cells, such as α-MEM, RPMI1640, ASF and S-clone. From the culture supernatant, a monoclonal antibody can be collected. Alternatively, an animal such as a nude mouse, from which a hybridoma is derived, is previously treated with pristane and a cell is intraperitoneally injected to the animal to allow ascites to accumulate. From the ascites, a monoclonal antibody can be collected.

As a method for collecting a monoclonal antibody from the supernatant and ascites, a customary method can be used. Examples thereof include salting-out by e.g., ammonium sulfate and sodium sulfate, chromatography, ion-exchange chromatography and affinity chromatography by e.g., protein A and protein G.

TRACP-5b in a specimen can be specifically detected with high sensitivity by an immunoassay using the monoclonal antibody of the present invention. Examples of a target specimen include blood, serum, plasma, a tissue such as bone taken and isolated from a subject.

Examples of the detection method in accordance with an immunoassay using the monoclonal antibody of the present invention include sandwich assay ELISA, chemiluminescent enzyme immunoassay (CLEIA), latex agglutination method (nephelometry or turbidimetry) and immunohistochemical staining.

Examples of an immunoassay by use of measurement of enzyme activity of TRACP-5b include an assay of immunologically measuring TRACP-5b in a specimen by allowing TRACP-5b in the specimen such as the serum to bind to the monoclonal antibody of the present invention; allowing an enzymatic substrate for TRACP-5b, for example, P-nitrophenylphosphate or a salt thereof, to enzymatically react with TRACP-5b which is bound; and measuring the activity of the enzyme. In the method, more specifically, TRACP-5b can be measured as follows. First, to the monoclonal antibody of the present invention, which is adsorbed to a solid support, the specimen to be measured is added; and TRACP-5b in the specimen is reacted with the antibody through an antigen-antibody reaction. In this manner, TRACP-5b binds to the antibody. Then, the solid support is washed with a cleaning solution to remove components which are contained in the specimen and not adsorbed to the antibody. Thereafter, to the reaction system, an enzymatic substrate for TRACP-5b, for example, p-nitrophenyl phosphate or a salt thereof, is added and TRACP-5b bound to the antibody is reacted with the substrate. After the enzymatic reaction is terminated with a reaction stop solution, the absorbance of a phenol produced by the reaction, for example, p-nitrophenol, is measured at a wavelength of usually 390 nm to 450 nm, and preferably 400 to 430 nm. Since the value of absorbance reflects the level of TRACP-5b enzyme activity, the TRACP-5b in the specimen can be measured based on the value.

In the present invention, as is apparent from the above description of the measurement method, the antibody is preferably used by binding it to a solid support. As the solid support, a solid support usually used in a solid phase immunoassay such as ELISA, is used, but the support is not particularly limited to it. Examples of the material for the solid support include polystyrene, polypropylene, polycarbonate, polyethylene, nylon and methacrylate. Examples of the form of a solid support include a plate, (magnetic) beads and latex particles.

To prepare an antibody adsorbed to a solid support, an antibody against TRACP-5b is bound to a solid support by use of direct or indirect physical bonding, a chemical bonding or affinity. The amount of antibody for use often falls within the range of 1 ng to 100 mg/ml.

In the case of chemiluminescent enzyme immunoassay (CLEIA) using (magnetic) beads as a solid support, e.g., reagents and kits usually used in the chemiluminescent enzyme immunoassay (CLEIA) can be used.

In the case of latex agglutination using latex particles as a solid support, e.g., reagents and kits usually used in latex agglutination can be used.

When the measuring method of the present invention is performed, a kit for use in immunoassay for TRACP-5b, containing i) a solid support and ii) the antibody(ies) of the present invention, can be used.

With respect to i) a solid support and ii) the antibody(ies) of the present invention in the kit, the solid support and a solution containing the antibody are separately prepared and the antibody may be adsorbed onto the solid support at the time of measuring TRACP-5b, or the antibody previously adsorbed onto the solid support may be provided. The kit preferably contains a cleaning solution for removing components not adsorbed to the solid support after TRACP-5b in a specimen is bound to the antibody. As the cleaning solution, for example, a Tris buffer containing a surfactant can be used.

The kit of the present invention can further add and contain a diluent for a specimen, if necessary. As the diluent for a specimen, for example, a buffer solution such as Tris can be used. The buffer solution may comprise, if necessary, a chelating agent such as EDTA.2Na and a mineral salt such as sodium chloride.

In the present invention, TRACP-5b can be measured by sandwich assay ELISA using the monoclonal antibody(ies) of the present invention. In this case, any other antibody against TRACP-5b except the antibodies of the present invention can be used as the monoclonal antibody. The method for measuring TRACP-5b in accordance with the sandwich assay is more specifically as follows. First, as a primary antibody, the antibody of the present invention is adsorbed onto a solid support such as a plate and reacted with TRACP-5b in a specimen such as serum. The solid support is washed. Then, TRACP-5b adsorbed is reacted with a biotinylated secondary antibody, for example, a biotinylated monoclonal or polyclonal antibody against TRACP-5b and then reacted with peroxidase-labeled streptavidin. Thereafter, a peroxidase enzyme reaction, and then, a chromogenic reaction, are carried out. In this manner, TRACP-5b can be detected. Alternatively, the same measurement can be carried out by using a secondary antibody to which an enzyme such as a peroxidase and an alkaline phosphatase is directly labeled. Furthermore, in the measuring method of present application, the substance to be coupled to a secondary (labeled) antibody is not limited to an enzyme. A radioactive isotope, a fluorescent substance, a magnetic material or colloid may be alternatively used as the substance to be coupled.

In the present invention, sandwich assay ELISA using the antibody(ies) of the present invention can be carried out by employing a kit for sandwich assay ELISA.

In the measuring method of the present invention carried out by sandwich assay ELISA, for example, an immunoassay kit for TRACP-5b, which contains i) a solid support, ii) the antibody(s) of the present invention, iii) a labeled antibody against another TRACP-5b and iv) a component for detecting the label, can be used for measuring TRACP-5b.

The component for detecting the label refers to a component for measuring a substance labeled with the antibody. If the label is biotin, a reagent, which contains peroxidase-labeled streptavidin, a peroxidase (enzyme) substrate, i.e., tetramethylbenzidine, and hydrogen peroxide, is used; whereas, if the label is an alkaline phosphatase, a reagent containing p-nitrophenyl phosphate is used. The kit, if necessary, may contain a cleaning solution.

If the kit is used in the present invention, the kit preferably contains a cleaning solution for removing components not adsorbed to a solid support, after TRACP-5b in a specimen is bound to the antibody. As the cleaning solution, for example, a Tris buffer containing a surfactant can be used. The kit of the present invention can further contain a diluent for a specimen, if necessary. As the diluent for a specimen, for example, a buffer solution such as Tris can be used. The buffer solution may comprise a chelating agent such as EDTA.2Na and a mineral salt such as sodium chloride, if necessary.

In the present invention, TRACP-5b present in a specimen can be detected by an immunohistochemical staining method using the monoclonal antibody of the present invention. More specifically, a frozen section is prepared from, for example, a human osteoclast tissue, by a routine method, reacted with the monoclonal antibody of the present invention, and subsequently reacted with, for example, a secondary antibody labeled with an enzyme such as a peroxidase and an alkaline phosphatase for color developing. In this manner, the presence of TRACP-5b can be specifically detected.

Detection by such an immunohistochemical staining method can be carried out by using a kit containing i) the monoclonal antibody of the present invention, ii) a labeled secondary antibody and iii) a color-developing reagent as components. Examples of the labeled secondary antibody include an animal-derived anti-IgG anti-serum and an anti-IgG polyclonal antibody labeled with an enzyme such as a peroxidase and an alkaline phosphatase. As the color-developing reagent, a reagent such as a chromogenic substrate usually used for developing an enzyme used as a label can be used.

In the present invention, chemiluminescent enzyme immunoassay (CLEIA) and latex agglutination using the antibody of the present invention can be carried out by using a chemiluminescent enzyme immunoassay (CLEIA) kit and a latex agglutination kit known in the art.

The epitope refers to a part of an antigen recognized by an antibody. Full-length TRACP-5 itself is constituted of 325 amino acids. An antibody does not recognize the whole TRACP-5 but recognizes only a relatively small portion of the antigen and bind to the portion. In order to serve as an epitope, the portion must have a length corresponding to at least 10 amino-acid residues, and more preferably, 5 amino acid residues. The antibody-binding portion is called "epitope" or also called "an antigenic determinant".

The phrase "recognizing an "epitope"" means that an antibody corresponding to an epitope portion can bind in the condition where the antigen containing the epitope either maintains a steric structure or loses the steric structure. In contrast, the phrase "does not recognize "epitope"" means that the corresponding antibody does not substantially bind in the condition where either the antigen maintains a steric structure or loses the steric structure.

In the present invention, the steric (conformational) structure refers to a secondary structure formed by folding a primary structure meaning an amino acid sequence, including a helix and a β-sheet; a three dimensional structure formed by further folding a polypeptide having a secondary structure; and a quaternary structure, i.e., a spatial configuration, formed by mutually associating a plurality of polypeptides having a tertiary structure, and preferably refers to a conformation of an antigen that may take in the in-vivo environment or a like-environment where the antigen is conceived to be usually present.

EXAMPLES

The present invention will be more specifically described by way of the following Examples, Comparative Examples and Reference Examples; however, the present invention is not limited by these Examples.

Example 1

(1) Selection and Preparation of Antigen for Producing a Monoclonal Antibody

As an antigen for producing an anti-human TRACP monoclonal antibody, recombinant TRACP-5b, which was produced in the silk gland of a genetic recombinant silkworm, was prepared. The recombinant TRACP-5b was prepared in accordance with the method described in Japanese Patent No. 5177431.

From a genetic recombinant silkworm containing a recombinant human TRACP-5b, the silk gland was excised out to obtain silk gland (300 g). The silk gland was suspended in 5600 mL of a buffer solution (50 mM Tris-HCl, pH7.5), homogenized by a rotor-stator homogenizer, and then centrifuged at 10,000 rpm, for 20 minutes. The resultant supernatant was applied to a CM-Sepharose column (40 mm in diameter×40 cm) (GE Healthcare) and the adsorbed protein was allowed to elute in a linear concentration gradient (0-1.0 M NaCl) with the Tris buffer containing NaCl. The tartaric acid resistant acid phosphatase activity was measured by using a substrate, p-nitrophenyl phosphate, and the fraction(s) exhibiting high activity was pooled. The pooled sample was concentrated, dialyzed against a 20 mM Tris buffer (pH7.2) containing 0.7 M NaCl and applied to Superdex S200 column (16 mm in diameter×60 cm) (GE Healthcare). The tartaric acid resistant acid phosphatase activity of the eluted fraction was measured in the same manner as above and the fraction(s) exhibiting activity was pooled. The fraction pooled was diluted twice with a 20 mM Tris buffer (pH7.2) and applied to HiTrap Heparin HP column (5 mL) (GE Healthcare). The adsorbed protein was subjected to a linear concentration gradient (0.35 M-1M NaCl), i.e., salt concentration gradient, with the 20 mM tris buffer (pH7.2) containing NaCl and eluted. The fraction(s) of the tartaric acid resistant acid phosphatase exhibiting high activity was pooled and concentrated to obtain purified recombinant human TRACP-5b (1.2 mg).

Note that, the amount of protein was checked at $A_{280}$ and the purity was checked based on the result of SDS-PAGE and silver staining, the result that a single band was obtained at a molecular weight of near 35,000. The enzyme appeared as a single band was used as purified TRACP-5b serving as an immunizing antigen.

(2) Immunity

Purified recombinant human TRACP-5b was diluted with 20 mM Tris-HCl, pH7.2 so as to obtain a concentration of 1 mg/ml. An aliquot of 50 μg (50 μl) was taken and mixed with 50 μl of Freund's complete adjuvant (WAKO) until emulsified. The suspension prepared was administered intraperitoneally to a Balb/c 6 week-old female mouse (CLEIA Japan, Inc) under anesthesia with diethyl ether. Two weeks later, the same amount of TRACP-5b (50 μg/ml) was mixed with Freund's incomplete adjuvant (WAKO) to prepare an emulsified suspension in the completely same operation as in the case of the Freund's complete adjuvant and sensitized the mouse respectively. Two weeks later, the similar operation was repeated. At the fourth times, a final immune containing TRACP-5b (50 μg/ml) was prepared with 20 mM Tris-HCl, pH7.2, and administered to the mouse by tail vein injection.

(3) Establishment of Hybridoma

Three days after the final immunization, the spleen was surgically excised out from the mouse sensitized to TRACP-5b under anesthesia with diethyl ether and aseptically dispersed to prepare spleen cells. The spleen cells were fused with myeloma cells P3-X63-Ag8-U1 (P3U1) in accordance with the Kohler and Milstein method (Nature. 256, 495, 1975) by use of polyethylene glycol (PEG4000) (MERK). The fusion ratio of the spleen cells ($8 \times 10^7$) to the myeloma cells P3-X63-Ag8-U1 (P3U1) ($2 \times 10^7$) was 4:1. The fused cells were scattered on 10% FCS (INVITROGEN) α-MEM (GIBCO)HAT (Cosmobio) medium, dispensed on a 48-well microtiter culture plate (Sumitomo Bakelite Co., Ltd) and cultured at 37° C. in the conditions of 5% $CO_2$. The number of hybridomas used in the following studies was 3000.

(4) Screening

About two weeks later, growth of the colony was checked and screening was carried out. How to perform screening will be described below.

A plate for screening was prepared by dissolving TRACP-5b purified in the above step (1) in a 20 mM Tris-HCl (pH7.2) buffer solution and dispensing the solution in a 96-well plate (Nunc) so as to be 0.5 μg/100 μl/well. The plate was allowed to stand still at 4° C. two nights and then washed three times with a Tris buffer containing 0.05% Tween-20. To this, 1.5% BSA solution (200 μl) was dispensed in order to suppress a non-specific reaction. The plate was further allowed to stand still at 4° C. overnight. The resultant plate was washed three times with a Tris buffer containing 0.05% Tween-20, then allowed to react with the culture supernatant (100 μl) and further washed. Thereafter, a secondary antibody, a HRP-labeled anti-mouse immunoglobulin antibody (INVITROGEN) was added and allowed to react. After washing, 100 μl of a chromogenic substrate for HRP, i.e., 3,3',5,5'-tetramethylbenzidine (TMB) (KAINOS LABORATORIES INC.), was added and allowed to stand still for a predetermined time. After color developing, 100 μl of 1N sulfuric acid was further added as a stop solution. Absorbance was measured at a measurement wavelength of 450 nm. The clones (29 clones) which gave a positive result in the above method was subjected to limiting dilution and again cloned. The supernatant was checked again.

(5) Verification of Antibody

The reactivity with purified TRACP-5b was checked by ELISA. As a result, clones TrK-126 and TrK-127 of the 29 clones reacted well with the plate even through the degree of affinity was different. Thus, clones TrK-126 and TrK-127 were selected as those recognizing TRACP-5b. The obtained antibodies were checked by a monoclonal antibody typing kit (ROCHE). The results are shown in Table 1 below.

TABLE 1

Table 1 characterization of clones

| Clone name | class | Light chain |
|---|---|---|
| TrK-126 | IgG1 | κ |
| TrK-127 | IgG1 | κ |

The above hybridomas TrK-126 and TrK-127 were received by the Patent Microorganisms Depositary (NPMD) in the National Institute of Technology and Evaluation (NITE Receipt Nos. NITE ABP-0 1866 (TrK-126) and NITE ABP-0 1867 (TrK-127)) as of Jun. 6, 2014, and confirmed as alive at Jun. 23, 2014. Thereafter, Deposit Accession Nos. NITE BP-0 1866 (TrK-126) and NITE BP-01867 (TrK-127) were given (deposition receipt was issued on Jun. 30, 2014).

The deposition is specified by the following descriptions.

[1] Name and Address of the Depositary

Name: Patent Microorganisms Depositary (NPMD), National Institute of Technology and Evaluation Address: 2-5-8, Kazusakamatari, Kisarazu-shi, Chiba 292-0818 Japan

[2] Deposition date: Jun. 6, 2014

[3] Accession number: NITE BP-01866 (hybridoma TrK-126)

NITE BP-01867 (hybridoma TrK-127)

(6) Preparation and Purification of Monoclonal Antibodies

Hybridomas TrK-126 and TrK-127 ($1 \times 10^7$ cells) obtained in the above step (5) each was intraperitoneally administered to a 10 week-old Balb/c female mouse (CLEIA Japan, Inc.) two weeks after 0.5 ml of pristane (Sigma Aldrich) was administered. About two weeks later, the ascites accumulated in the mouse abdominal cavity was surgically taken under anesthesia with diethyl ether. The ascites was used as a sample, serially diluted and checked by the ELISA used for screening in the above step (4). As a result, it was found that a monoclonal antibody was contained in a high concentration. The ascites was treated with 40% ammonium sulfate, dialyzed against PBS, then purified by protein G column (GE Healthcare) and checked by SDS-PAGE. As a result, both in TrK-126 and TrK-127, a single band was observed at a molecular weight of about 150,000 in a non-reduced condition; and two bands were observed at a molecular weight of about 50,000 and 25,000, respectively, in a reduced condition with mercaptoethanol. The amounts of purified antibodies in the cases of TrK-126 and TrK-127 were both about 10 mg or more per mouse and sufficient for industrial use.

(7) Measurement of TRACP-5b by the Sandwich ELISA and Verification of Specificity A reagent for measuring TRACP-5b according to sandwich ELISA were prepared by using monoclonal antibodies TrK-126 and TrK-127. To check specificity of the measurement method, the following experiment was carried out by using Native-TRACP-5b and TRACP-5a and compared to the results of sandwich ELISA of TRACP-5b using monoclonal antibodies TrK-62 and TrK-49 (Japanese Patent No. 4164804). The measuring method is as follows.

On a solid plate (Nunc), monoclonal antibody TrK-126 purified by using Protein G was dispensed so as to be a concentration of 2 µg/well and allowed to stand still at 4° C. for 2 days. The plate was washed three times with a 20 mM Tris (pH7.5) cleaning solution containing 0.05% Tween 20, and thereafter, 200 µL of 1.5% BSA Tris (pH7.5) was added thereto and allowed to stand still at 4° C. overnight for blocking. A labeled antibody was prepared by labelling monoclonal antibody TrK-127, which was purified in the same manner as mentioned above, with ALP by use of HRP Labeling Kit-NH2 (Dojindo Laboratories). The concentration of labeled antibody herein was specified as 1 µg/µl.

Using the plate and the labeled antibody thus prepared, usefulness of sandwich ELISA for measuring TRACP-5b was evaluated. More specifically, 50 µl of a human serum-derived TRACP-5b sample (the content of TRACP-5b was computationally determined) was added to an antibody-bound plate. A reaction was allowed to proceed at room temperature for one hour. After completion of the reaction, the plate was washed three times with the cleaning solution as mentioned above and 100 µl of a secondary antibody labeled with horseradish peroxidase (HRP) was added. A reaction was further allowed to proceed at room temperature for one hour. After completion of the reaction, the plate was washed three times with the cleaning solution as mentioned above and 100 µl of 3,3',5,5'-tetramethylbenzidine (TMB) (KAINOS LABORATORIES INC.) was added. After the plate was allowed to stand still for a predetermined time for color developing, 100 µl of 1N sulfuric acid was added as a stop solution. Absorbance was measured at a measurement wavelength of 450 nm.

As a result of the measurement, in the measurement system using the antibodies obtained in the present invention, it was verified that absorbance increases depending upon the concentration of TRACP-5b (FIG. 1).

Similarly, a sample (50 µl) prepared so as to contain human serum-derived TRACP-5b alone in a final concentration of 25 ng/mL, or a sample (50 µl) prepared so as to contain TRACP-5b and TRACP-5a each in a final concentration of 25 ng/mL was added onto the antibody-bound plate. A reaction was allowed to proceed at room temperature for one hour. After completion of the reaction, the plate was washed three times with the cleaning solution as mentioned above and 100 µl of a secondary antibody labeled with horseradish peroxidase (HRP) was added. A reaction was further allowed to proceed at room temperature for one hour. After completion of the reaction, the plate was washed three times with the cleaning solution as mentioned above and 100 µl of 3,3',5,5'-tetramethylbenzidine (TMB) (KAINOS LABORATORIES INC.) was added. After the plate was allowed to stand still for a predetermined time for color developing, 100 µl of 1N sulfuric acid was further added as a stop solution. Absorbance was measured at a measurement wavelength of 450 nm.

Figure 2:
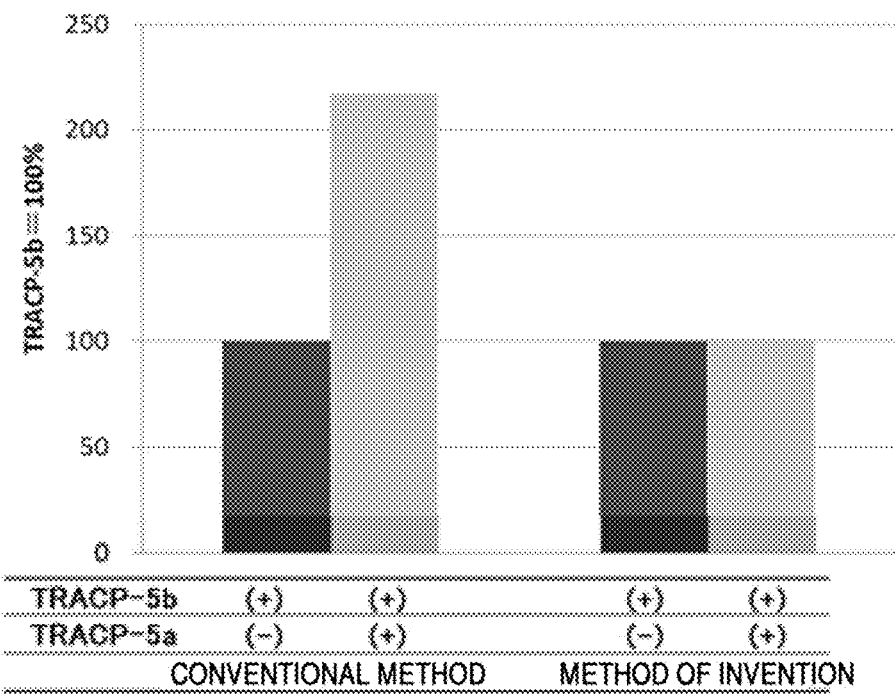
FIG. 2 shows verification of specificity by ELISA.

As a result of the measurement, it was verified that the known sandwich ELISA for TRACP-5b (Japanese Patent No. 416804) showed a reactivity to both native TRACP-5b and TRACP-5a; whereas the sandwich ELISA by using TrK-126 and TrK-127 (FIG. 2) showed a reactivity specific to TRACP-5b.

(8) Measurement of TRACP-5b by Chemiluminescent Enzyme Immunoassay (CLEIA)

A reagent for measuring TRACP-5b using magnetic beads was prepared by using monoclonal antibodies TrK-126 and TrK-127. To check specificity of the measurement method of the invention, a reagent for measuring was prepared by using the antibody used in the publicly-known method (Japanese Patent No. 416804) in the same manner as above. Native TRACP-5b and TRACP-5a were compared for reactivity. The measuring method is as follows.

5 mg of TrK-126 or TrK-62 was conjugated to magnetic beads by Dynabeads Antibody Coupling Kit (INVITROGEN). A labeled antibody was prepared by labelling 200 µg of TrK-127 or TrK-49 with ALP by use of Alkaline Phosphatase Labeling Kit-NH2 (Dojindo Laboratories). The concentration of the labeled antibody was specified as 1 µg/µl.

Using the magnetic beads and the labeled antibody prepared in the above, usefulness of chemiluminescent enzyme immunoassay (CLEIA) for measuring TRACP-5b was evaluated. More specifically, 30 µl of a human serum sample (the content of TRACP-5b was computationally obtained) was added to 2 µg of an antibody-conjugated magnetic beads. The mixture was stirred for about 20 minutes. While collecting magnetic beads by a magnet, the magnetic beads were washed three times with a 20 mM Tris (pH7.5) cleaning solution containing 0.05% Tween 20, and then 0.05% Tween 20-containing 20 mM Tris (pH7.5) containing the 1 µg of ALP labeled antibody was added. The mixture was stirred for 20 minutes. While collecting magnetic beads by a magnet, the magnetic beads were washed three times with a 20 mM Tris (pH7.5) cleaning solution containing 0.05% Tween 20, and thereafter, 100 µl of substrate for ALP, i.e., AMPPD (Wako Pure Chemical Industries Ltd.), was added. The mixture was stirred for about 5 minutes at room temperature and the emission amount of light having an emission maximum at a wavelength of 477 nm was measured.

Figure 3:
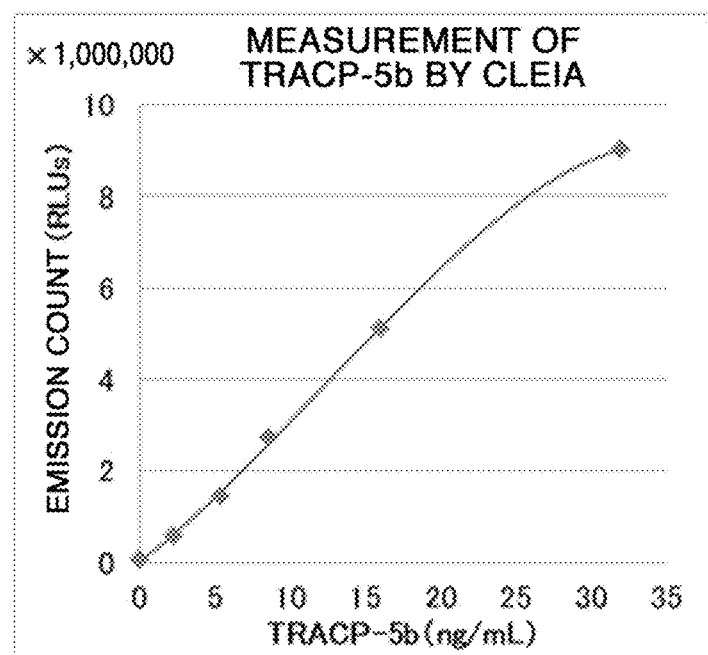
FIG. 3 shows measurement of TRACP-5b by CLEIA.

As a result of the measurement, in the measurement system using the antibody(s) obtained in the present invention, it was found that the count of light emission increases depending upon the concentration of TRACP-5b (FIG. 3).

Similarly, to a sample (30 µl) containing human serum-derived TRACP-5b alone in a final concentration of 25 ng/mL, or a sample (30 µl) containing TRACP-5b and TRACP-5a each in a final concentration of 25 ng/mL, 2 µg of antibody-conjugated magnetic beads were added. The mixture was stirred for about 20 minutes. While collecting magnetic beads by a magnet, the magnetic beads were washed three times with a 20 mM Tris (pH7.5) cleaning solution containing 0.05% Tween 20 and thereafter, 0.05% Tween 20 containing—20 mM Tris (pH7.5) containing 1 µg of ALP labeled antibody was added thereto. The mixture was stirred for about 20 minutes. While collecting magnetic beads by a magnet, the magnetic beads were washed three times with a 20 mM Tris (pH7.5) cleaning solution containing 0.05% Tween 20. Then 100 µl of substrate for ALP, i.e., AMPPD (Wako Pure Chemical Industries Ltd.), was added and stirred for about 5 minutes at room temperature. The emission amount of light having an emission maximum at a wavelength of 477 nm was measured.

Figure 4:
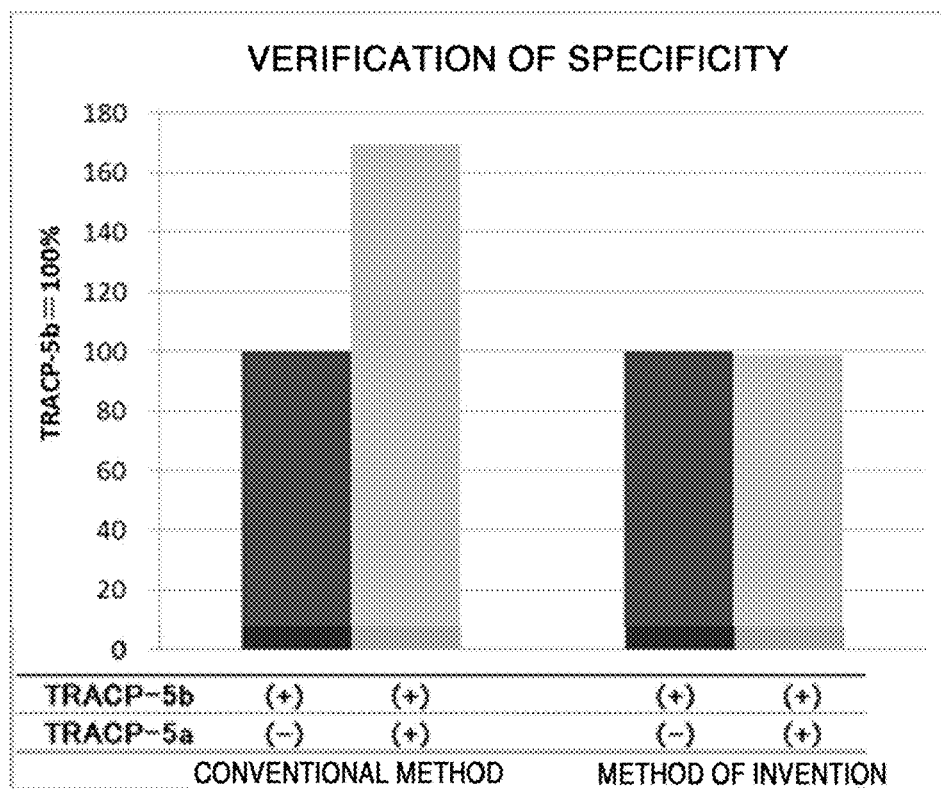
FIG. 4 shows verification of specificity by CLEIA.

As a result of the measurement, it is verified that reactivity to both of Native-TRACP-5b and TRACP-5a was found in the publicly-known measurement method (Japanese Patent Registration No. 416804); whereas the reactivity specific to TRACP-5b was found in sandwich ELISA by TrK-126 and TrK-127 (FIG. 4).

(9) Measurement of TRACP-5b by Latex Agglutination

A latex reagent was prepared by using monoclonal antibodies TrK-126 and TrK-127 to sensitize latex with two types of monoclonal antibodies. The latex reagent was prepared as follows.

A 1% latex suspension (2 mL) and a 0.1 mg/mL TrK-126 and TrK-127 antibody solution (2 mL) were mixed and stirred for about one hour. After centrifugation, the resultant precipitate was suspended in a 1% BSA solution and stirred again for about one hour. After the suspension solution was centrifuged again, the resultant precipitate was suspended in a PBS solution to obtain the latex reagent.

A peptide consisting of 20 to 325A. A was divided into small peptides each consisting of 10 A.A. Formation of spots of the peptides of 10 A.A. was asked to HT Peptide Slide Service (Replitope, Funakoshi) (Table 2; SEQ. ID No. 2 to 61).

TABLE 2

Peptide construction

| 01) DGATPALREV | 03) AVGDWGGVPN | 05) APFHTAREMA | 07) NAKEIARTVQ | 09) ILGADFILSL |
|---|---|---|---|---|
| 02) ALRFVAVGDW | 04) GGVPNAPFHT | 06) AREMANAKEI | 08) ARTVQILGAD | 10) FILSLGDNFY |
| 11) GDNFYFTGVQ | 13) DINDKRFQET | 15) FEDVFSDRSL | 17) RKVPWYVLAG | 19) NHDHLGNVSA |
| 12) FTGVQDINDK | 14) RFQETFEDVF | 16) SDRSLPKVPW | 18) YVLAGNHDHL | 20) GNVSAQIAYS |
| 21) QIAYSKISKR | 23) WNFPSPFYRL | 25) HFKIPQTNVS | 27) VAIFMLDTVT | 29) LCGNSDDFLS |
| 22) KISKRWNFPS | 24) PFYRLHFKIP | 26) QTNVSVAIFM | 28) LDTVTLCGNS | 30) DDFLSQQPER |
| 31) QQPERPRDVK | 33) LARTQLSWLK | 35) KQLAAAREDY | 37) VLVAGHYPVW | 39) SIAHGPTHC |
| 32) PRDVKLARTQ | 34) LSWLKKQLAA | 36) AREDYVLVAG | 38) HYPVWSIAEH | 40) GPTHCLVKQL |
| 41) LVKQLRPLLA | 43) TYGVTAYLCG | 45) HDHNLQYLQD | 47) EVGVGYVLSG | 49 AGNFMDPSKR |
| 42) RPLLATYGVT | 44) AYLCGHDHNL | 46) QYLQDENGVG | 48) YVLSGAGNFM | 50 SPSKRHQRKV |
| 51) HQRKVPNGYL | 53) RGSYGTEDSL | 55) GGFAYVEISS | 57) KEMTVTYIEA | 59) SGKSLFKTRL |
| 52) PNGYLRFHYG | 54) TEDSLGGFAY | 56) VEISSKEMTV | 58) TYIEASGKSL | 60 FKTRLPRRARP |

It was verified that TRACP-5b in a human serum can be quantified by use of the latex reagent prepared above in accordance with latex immunoagglutination measurement (LATEX measurement).

Figure 5:
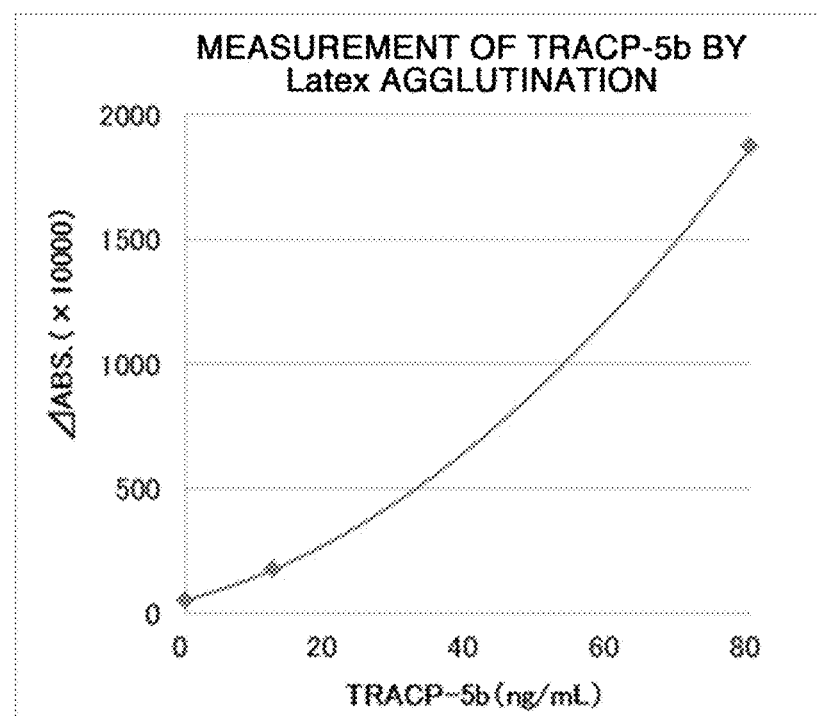
FIG. 5 shows measurement of TRACP-5b by latex agglutination.

To describe the measurement more specifically, a reagent-1 (100 μl) containing a Tris buffer and a reagent-2 (100 μl) containing the latex reagent prepared were allowed to react with a human serum sample (35 μl) (the content of TRACP-5b was computationally obtained). The amount of change in absorbance was obtained by measuring absorbance at two points, 19 and 34 light measurement points (corresponding to time points of 1 minute and 5 minutes after the second reagent was added) at a main wavelength 570 nm and a side wavelength of 800 nm in accordance with the 2 point end method, by use of Hitachi Type 7180 automatic analyzer. As a result, it was verified that absorbance increased depending upon the concentration of TRACP-5b, as shown in FIG. 5.

Comparative Example 1

Identification of Epitopes of TrK-62 and TrK-49
(1) Preparation of Peptide Slide (Replitope)
The ACP5 (TRACP-5) amino acid sequence (SEQ. ID No. 1) obtained from the NCBI database and various possible modification sites thereof reported in literatures are shown in FIG. 6.

(2) Analysis for Epitopes of TrK-62 and TrK-49 by Replitope

The peptide slides prepared were subjected to epitope mapping using TrK-62 and TrK-49 and analyzed by a chromogenic method (FIG. 7).

More specifically, the peptide slides were subjected to a blocking treatment using SUPERBLOCK (PIERCE) (a blocking reagent containing phosphate-buffered saline and a blocking protein) at room temperature for 60 minutes. Thereafter, a primary antibody, i.e., TrK-62 or TrK-49 (a concentration of 1 μg/mL) was allowed to react at room temperature for 60 minutes. After the slides were washed three times with PBS-T, rabbit mouse IgG-HRP (DAKO) (concentration: 0.5 μg/mL) was reacted at room temperature for 60 minutes. After the slides were washed three times with PBS-T again, a chromogenic substrate for HRP, i.e., 3,3',5,5'-tetramethylbenzidine (TMB) (KAINOS LABORATORIES INC.), was added. After incubation was carried out in a predetermined time, the degree of color developing from spots was observed by a microscope.

As a result of the analysis, it was found that both TrK-62 and TrK-49 recognize epitopes near the binding sites of a sugar chain specifically present in TRACP-5b. It was considered that specificity of a reaction with TRACP-5b is enhanced by this (FIG. 8).

Example 2

Epitope Analysis of TrK-126 and TrK-127

(1) Epitope Analysis of TrK-126 and TrK-127 by Replitope

In consideration of the above results, epitopes of TrK-126 and TrK-127 were analyzed by the luminescent method.

More specifically, the peptide slides were subjected to a blocking treatment using SUPERBLOCK (PIERCE) (a blocking reagent containing phosphate-buffered saline and a blocking protein) at room temperature for 60 minutes. Thereafter, a primary antibody, i.e., TrK-126 or TrK-127 (a concentration of 1 μg/mL) was allowed to react at room temperature for 60 minutes. After the slides were washed three times with PBS-T, a secondary antibody attached to AMERSHAM ECL PRIME (GE Healthcare) (a luminol-based Western blotting reagent) was added and a reaction was carried out at room temperature for 60 minutes. The slides were washed three times with PBS-T again, a detection reagent attached to a kit was added. After incubation was carried out for a predetermined time, the degree of luminescent from spots was checked by IMAGEQUANT LAS4000 (GE Healthcare) (a cooled CCD camera system).

Figure 9:
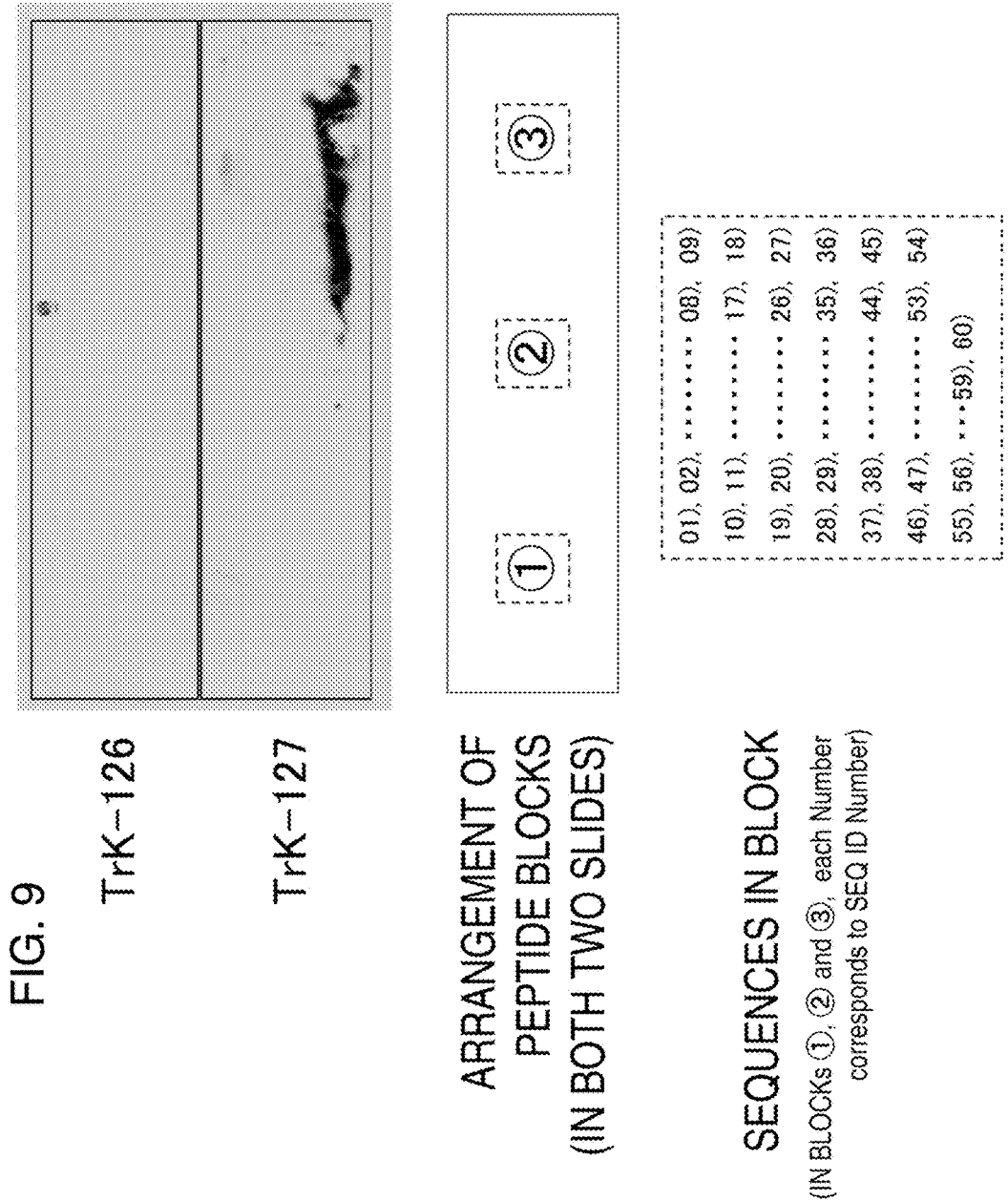
FIG. 9 shows epitope mapping of Trk-126 and Trk-127.

As a result of the analysis, neither TrK-126 nor TrK-127 had reactivity to each peptide sequence (FIG. 9). Then, dot blot analysis and western blot analysis using these two antibodies were carried out.

(2) Verification of Reactivity by Western Blot Method and Dot Blot Method (2-1) Verification of Reactivity by Dot Blot Method 1.0 μg of Purified TRACP-5b was dropped to a PVDF membrane (Millipore) and blocking was carried out for one hour. Subsequently, TrK-126 and TrK-127 (PBS-T containing an antibody at a concentration of 5 μg/ml) were separately reacted with the membrane having dots transferred thereon for one hour. After the reaction, the membrane was washed with PBS-T, a HRP-labeled anti-mouse immunoglobulin antibody (Zymed) serving as a secondary antibody was allowed to react individually for 30 minutes. After the membrane was washed with PBS-T, detection was made by a TMB solution (Wako Pure Chemical Industries Ltd.) for membrane (FIG. 10).

(2-2) Verification of Reactivity by Western Blot Method 1.0 μg or 2.0 μg of purified TRACP-5b was subjected to SDS-PAGE in a non-reducing condition. Thereafter, the resultant TRACP-5b was transferred to a PVDF membrane (Millipore) and blocking was carried out for one hour. Thereafter, reaction and detection were carried out in the same manner as described in step (2-1) (FIG. 11).

As a result of these analyses, the reactivity of TrK-126 and TrK-127 to TRACP-5b by dot blot method was found; whereas the reactivity of either TrK-126 or TrK-127 was not detected by western blot method. From these results, it was considered that TrK-126 and TrK-127 recognize the native steric (conformational) structure per se of TRACP-5b; and that the epitopes of TrK-126 and TrK-127 antibodies cannot be any of epitopes formed of a primary structure of a linear sequence but can be epitopes constituted of steric (conformational) structures of TRACP-5b.

TRACP-5a and TRACP-5b have high homology in the primary structure but greatly differ in three-dimensional shape. Thus, it is considered that an antibody recognizing an epitope constituted of a steric (conformational) structure of TRACP-5b is improved in TRACP-5b binding specificity in comparison with TrK-62 and TrK-49 (the linear sequence of the epitopes thereof are also present in TRACP-5a) used in the publicly-known measurement method (Japanese Patent Registration No. 416804).

INDUSTRIAL APPLICABILITY

As described in the above, the immunoassay of the present invention can specifically and accurately measure a target substance while eliminating effects of competitive substances in a reaction system by using antibodies having high reactivity and selectivity to a target substance to be measured (TRACP-5b), in combination.

---

The invention claimed is:

1. A monoclonal antibody which recognizes an epitope based on a steric structure of TRACP-5b (Tartrate-Resistant Acid Phosphatase 5b); which does not recognize any of epitopes formed of a primary structure of linear sequence of TRACP-5b; and which does not bind to TRACP-5a (Tartrate-Resistant Acid Phosphatase 5a), wherein said antibody is produced by Hybridoma TrK-126 of Accession number NITE BP-01866 or Hybridoma TrK-127 of Accession number NITE BP-01867.

2. Hybridoma TrK-126 of Accession number NITE BP-01866.

3. Hybridoma TrK-127 of Accession number NITE BP-01867.

4. A kit for use in detection of TRACP-5b (Tartrate-Resistant Acid Phosphatase 5b), comprising the monoclonal antibody produced by Hybridoma TrK-126 of Accession number NITE BP-01866 and the monoclonal antibody produced by Hybridoma TrK-127 of Accession number NITE BP-01867; wherein each of these monoclonal antibodies recognizes an epitope based on a steric structure of TRACP-5b;
   does not recognize any of epitopes formed of a primary structure of linear sequence of TRACP-5b; and
   does not bind to TRACP-5a (Tartrate-Resistant Acid Phosphatase 5a),
as constituents.

* * * * *